(12) United States Patent
Shirai et al.

(10) Patent No.: US 8,057,455 B2
(45) Date of Patent: Nov. 15, 2011

(54) SHORTS TYPE DISPOSABLE DIAPER

(75) Inventors: Atsuko Shirai, Sakura (JP); Akira Kamori, Sakura (JP); Takeda Masamichi, Sakura (JP)

(73) Assignee: Daio Paper Corporation, Ehime (JP)

( * ) Notice: Subject to any disclaimer, the term of this patent is extended or adjusted under 35 U.S.C. 154(b) by 1087 days.

(21) Appl. No.: 11/791,880

(22) PCT Filed: Oct. 28, 2005

(86) PCT No.: PCT/JP2005/019881
§ 371 (c)(1),
(2), (4) Date: Jul. 2, 2007

(87) PCT Pub. No.: WO2006/059443
PCT Pub. Date: Jun. 8, 2006

(65) Prior Publication Data
US 2008/0027406 A1    Jan. 31, 2008

(30) Foreign Application Priority Data

| Nov. 30, 2004 | (JP) | ................. | 2004-346050 |
| Nov. 30, 2004 | (JP) | ................. | 2004-346131 |
| Nov. 30, 2004 | (JP) | ................. | 2004-346139 |
| Dec. 24, 2004 | (JP) | ................. | 2004-373216 |
| Jan. 31, 2005 | (JP) | ................. | 2005-023288 |

(51) Int. Cl.
*A61F 13/15* (2006.01)
*A61F 13/20* (2006.01)

(52) U.S. Cl. ............................. 604/385.27; 604/385.24

(58) Field of Classification Search . 604/385.24–385.27
See application file for complete search history.

(56) References Cited

FOREIGN PATENT DOCUMENTS

| JP | 2000-14700   | 1/2000 |
| JP | 2001-204762  | 7/2001 |
| JP | 2001-258931  | 9/2001 |
| JP | 2003-19163   | 1/2003 |
| JP | 2003-102779  | 4/2003 |
| JP | 2003-126148  | 5/2003 |
| JP | 2004-254862  | 9/2004 |

OTHER PUBLICATIONS

English translation of specification for JP 2001-204672 to Takahata et al.*
English translation of specification for JP 2000-014700 A to Miyata et al.*

* cited by examiner

*Primary Examiner* — Melanie Hand
(74) *Attorney, Agent, or Firm* — Jordan and Hamburg LLP

(57) ABSTRACT

An outer packaging sheet in a paper diaper is provided with: hip elastic bands including a plurality of hip elastic members arranged from one joint end portion individually at a front and at a back to the other joint end portion; curved elastic bands including a plurality of curved elastic members extending from one of the joint end portions individually at the front and at the back to the side of a crotch portion and arranged over the other joint end portion while bypassing that crotch portion; and an absorbent body arranged in the crotch portion. The curved elastic bands are formed to cover such areas of the outer packaging sheet substantially as are enclosed by the edge portions of the outer packaging sheet, the absorbent body and the hip elastic bands.

16 Claims, 18 Drawing Sheets

Fig. 19
ADHESIVE INTERVAL: RUBBER INTERVAL = 1 : 2
Fig. 19(A)
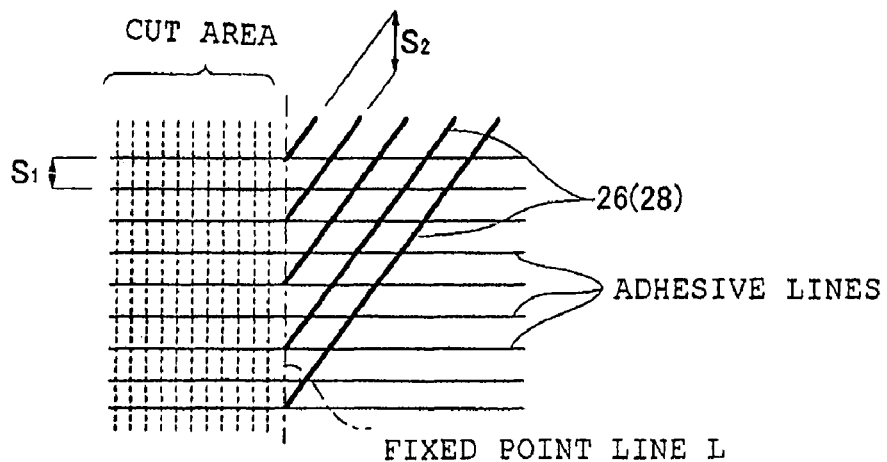
Fig. 19(B)
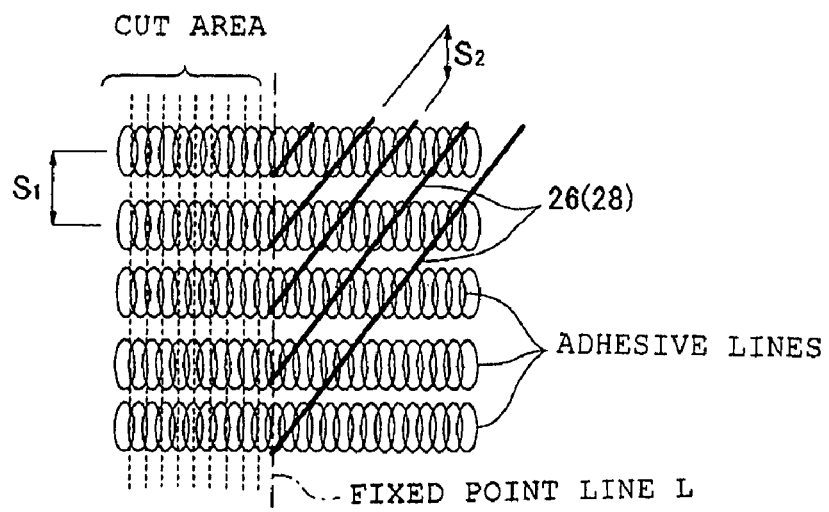
Fig. 19(C)
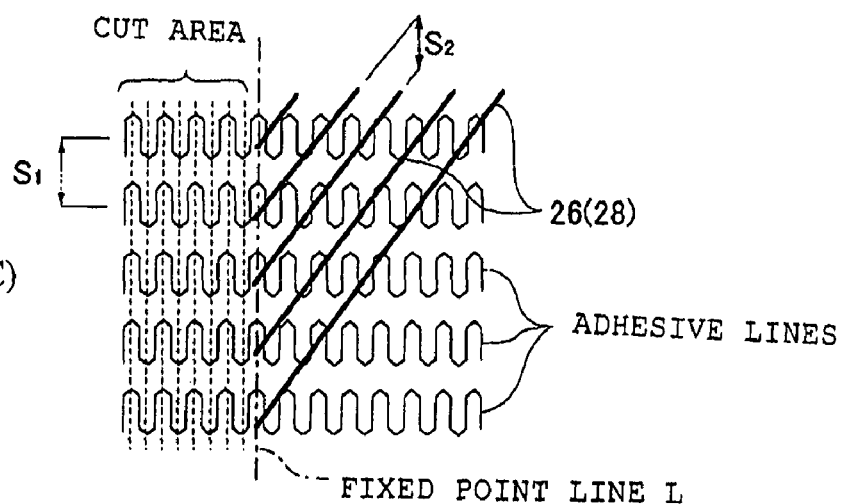

Related art

Related art

SHORTS TYPE DISPOSABLE DIAPER

BACKGROUND OF THE INVENTION

The present invention relates to a pants type disposable diaper, which is improved in wearability and fitness.

In the pants type disposable diaper of the prior art, in order to mount a bodily fluid absorber properly on a body, an elastically stretchable member is arranged in an outer packaging sheet for holding that absorber, thereby to improve the fit on the body.

As shown in FIG. 21, for example, there is known (as referred to Patent Document 1, for example) a pants type disposable diaper comprising a diaper body 50 having an absorber 40 sandwiched between a top sheet and a back sheet. The diaper body includes waist elastic members 51 arranged in a front 50F and a back 50B forming a waist opening, and leg elastic members 52, 52, . . . , and so on, which are curved to bulge individually from the front 50F and the back 50B to a substantially central side of a crotch portion 50C and arranged along the edge portions of the diaper body 50 to form the leg openings.

As shown in FIG. 22, moreover, there is known (as referred to Patent Document 2, for example) a pants type disposable diaper, in which a plurality of elastically stretching members 61, 61, . . . , and so on are arranged individually on the sides of the front and the back of a diaper body 60, and in which the elastically stretching members are curved to bulge from the side of the waist opening to the side of the crotch portion as they go from the side of the waist opening to the side of the crotch portion.

Patent Document 1: JP-A-2001-258931
Patent Document 2: JP-A-2001-204762

In the case of Patent Document 1, however, the leg elastic members 52 are arranged along the edge portions of the diaper body 50 forming the leg openings so that the leg openings can be fitted on the wearer of the diaper by the shrinking force of the leg elastic members 52. However, a generally triangular area Tr in the outer packaging sheet, which is defined by the leg elastic members 52, the waist elastic members 51 and the absorber 40 and which is composed of a top sheet and a back sheet, is shrunken at its periphery by the leg elastic members 52 and the waist elastic members 51. In the product state, therefore, the generally triangular area Tr is shaped to bulge on its inner side thereby to form a pocket-shaped space on the inner side of the diaper.

When this pants type disposable diaper is removed or put on, there arises a problem that the toes or heels may be caught by that pocket-shaped space thereby to obstruct the removing or donning of the diaper.

In the case of Patent Document 2, on the other hand, of the plural elastically stretching members 61, 61, . . . , and so on, the elastically stretching members on the side of the crotch portion are curved to fit the diaper itself or the diaper absorber is fitted on the body. However, the shrinking force of the elastically shrinking members 61 to act as an action force to stabilize the diaper around the hip is weakened to raise a problem that the diaper easily slips off the hip.

Moreover, the user of the pants type disposable diaper (or the paper diaper) may have his or her power weakened because of influences of the age, disease or handicap, thereby to have a weak hand power or to fail to bring his or her arms sufficiently to the back or buttocks.

When such user uses the paper diaper, moreover, he or she may have to wear the paper diaper around the hip by grasping and pulling up the front or sides of the paper diaper. In the case of the paper diaper of the prior art, as shown in FIG. 23, the waist portion of the back of the paper diaper may be caught by the bulges of the buttocks and insufficiently pulled up, and may be worn in an incomplete state. Moreover, the incomplete wear of the paper diaper and the incomplete fit on the hip may cause the leakage of the bodily fluid such as urine.

An object of the invention is to provide a pants type disposable diaper, which can be worn easily and properly.

SUMMARY OF THE INVENTION

In order to solve the aforementioned problems, according to a first aspect of the invention, there is provided a pants type disposable diaper comprising: an absorbent body including an absorber; and an outer packaging sheet formed integrally on the outer face side of the absorbent body, wherein the front and back in the outer packaging sheet in a product state are jointed at the joint end portions of their two side ends thereby to form a waist opening and a pair of left and right leg openings, characterized:

in that the absorbent body is disposed in a crotch portion formed to extend from the front to the back of the outer packaging sheet recessed more than the absorbent body to the outer sides of a width direction; and in that the outer packaging sheet includes hip elastic bands having a plurality of hip elastic members extending from one of joint end portions to the other joint end portion at the front and the back and arranged generally in parallel with each other at a vertical spacing, and curved elastic bands having a plurality of curved elastic members extending to the side of the crotch portion from one joint end portion of at least one of the front and the back and arranged to extend to the other joint end portion while bypassing the crotch portion, the curved elastic bands being formed to cover substantially the whole area of the outer packaging sheet, which is defined by the edge portions of the outer packaging sheet, the absorbent body and the hip elastic bands.

According to the first aspect of the invention, the outer packaging sheet of the pants type disposable diaper includes waist elastic bands having a plurality of waist elastic members extending from one of joint end portions to the other joint end portion at the front and the back and arranged, curved elastic bands having a plurality of curved elastic members extending to the side of the crotch portion from one joint end portion of at least one of the front and the back and arranged to extend to the other joint end portion while bypassing the crotch portion, and the absorbent body arranged in the crotch portion.

Moreover, the curved elastic bands are formed to cover substantially the whole area of the outer packaging sheet, which is defined by the edge portions of the outer packaging sheet, the absorbent body and the hip elastic bands. As a result, the areas of the outer packaging sheet are substantially homogeneously shrunken as a whole by the curved elastic bands so that those areas are prevented unlike the prior art from bulging on their inner sides and from forming pocket-shaped spaces. If the pocket-shaped space, as would obstruct the wearing action, is not on the inner side of the pants type disposable diaper (outer packaging sheet), the wearer hardly has, when he or she puts on or removes the pants type disposable diaper, toes or heels caught by the inner side of the pants type disposable diaper, so that he or she can put on or remove the pants type disposable diaper easily.

Moreover, the pants type disposable diaper is provided, separately of the curved elastic bands (or the curved elastic members), with the hip elastic bands (or the hip elastic members) at the front and the back corresponding to the hip of the body in addition to the curved elastic bands (or the curved elastic members), so that the pants type disposable diaper can be so stably mounted around the hip as not to tend to slip down. Thus, this pants type disposable diaper serves as the properly wearable pants type disposable diaper.

According to a second aspect of the invention, there is provided a pants type disposable diaper as set forth in the first aspect of the invention, characterized in that the back is provided with the curved elastic bands.

The second aspect of the invention attains an effect similar to that of the first aspect of the invention. Especially, the back is provided with the curved elastic bands. Even in case the diaper user pulls up the pants type disposable diaper by grasping the front with his or her single hand, the action force to act on the front is transmitted through the joint end portion to the curved elastic band of the back, so that he or she can pull up the pants type disposable diaper such that the back covers the buttocks properly thereby wear the pants type disposable diaper properly around the hip.

In short, the curved elastic bands are curved to the sides of the crotch portion so that the action force transmitted to the curved elastic band of the back acts to pull up the back of the pants type disposable diaper from the lower side. Even if, therefore, the user of the pants type disposable diaper has a weak arm power or cannot stretch his or her arms sufficiently to the back or the buttocks, he or she is enabled to pull up the back thereby to cover the buttocks by grasping and pulling up the easily graspable front side of the pants type disposable diaper. Thus, the user can wear the pants type disposable diaper properly.

According to a third aspect of the invention, there is provided a pants type disposable diaper according to the first aspect of the invention, characterized in that the front and the back are provided with the curved elastic bands.

The third aspect of the invention attains an effect similar to that of the first aspect of the invention. Especially the front and the back are provided with the curved elastic bands. As a result, the wear obstructing pocket-shaped space on the inner side of the pants type disposable diaper (or the outer packaging sheet) disappears from both the front and the back.

Thus, when the user wears and removes the pants type disposable diaper, the toes or heels do not tend to be caught by the inner side so that the pants type disposable diaper is made more wearable.

Moreover, the curved elastic bands are curved to the crotch portion side, so that they act to pull up the pants type disposable diaper from the lower side when the action force to pull up the pants type disposable diaper is transmitted to the curved elastic bands. Even if, therefore, the user of the pants type disposable diaper has a weak hand power or cannot stretch his or her arms sufficiently to the back side or buttock side, the pants type disposable diaper can be pulled to fit the hip by pulling up its easily graspable front side. As a result, the user can wear the pants type disposable diaper properly.

According to a fourth aspect of the invention, there is provided a pants type disposable diaper according to any of the first to third aspects of the invention, characterized in that the spacing of the curved elastic members constituting the curved elastic bands is 20 mm or less in the area of the outer packaging sheet, which is defined by the edge portions of the outer packaging sheet, the absorbent body and the hip elastic bands.

According to the invention as set forth in the fourth aspect of the invention, the spacing of the curved elastic members of the curved elastic bands is 20 mm or less in the generally triangular areas of the outer packaging sheet, which is defined by the edge portions of the outer packaging sheet, the absorbent body and the hip elastic bands. By setting the spacing of the curved elastic members at 20 mm or less, preferably at 15 mm or less, more preferably at 9 mm or less, the toes are not caught between the curved elastic members, when the feet are smoothly threaded through the leg openings so as to wear the diaper.

According to a fifth aspect of the invention, there is provided a pants type disposable diaper according to any of the first to fourth aspects of the invention, characterized in that, in the area of the outer packaging sheet, which is defined by the edge portions of the outer packaging sheet, the absorbent body and the hip elastic bands, the curved elastic bands are formed over an area of at least 30 mm in the normal direction from the curved elastic members the closest to the leg openings.

According to the fifth aspect of the invention, in the generally triangular areas of the outer packaging sheet, which is defined by the edge portions of the outer packaging sheet, the absorbent body and the hip elastic bands, the curved elastic bands are formed over an area of at least 30 mm, or preferably 50 mm or more in the normal direction from the curved elastic members the closest to the leg openings. In other words, if the width of the curved elastic members is retained more than the aforementioned numerical values in the triangular areas, it is possible to exhibit the effects of the first to third aspects of the invention sufficiently. If the width of the curved elastic bands is retained at or more than the numerical values, there may exist the outer packaging sheet, in which the curved elastic members are not arranged in the triangular areas at the areas on the inner side of the curbed elastic bands.

According to a sixth aspect of the invention, there is provided a pants type disposable diaper according to any of the first to fifth aspects of the invention, characterized in that the curved elastic bands are constituted of at least four curved elastic members.

According to the sixth aspect of the invention, the curved elastic bands are constituted of at least four, preferably six or more preferably eight curved elastic members.

According to a seventh aspect of the invention, there is provided a pants type disposable diaper according to any of the first to sixth aspects of the invention, characterized in that, in the area of the outer packaging sheet, which is defined by the edge portions of the outer packaging sheet, the absorbent body and the hip elastic bands, the area ratio occupied by the curved elastic bands is 70% or more in the areas of the outer packaging sheet.

According to the seventh aspect of the invention, in the generally triangular areas of the outer packaging sheet, which is defined by the edge portions of the outer packaging sheet, the absorbent body and the hip elastic bands, the area ratio occupied by the curved elastic bands is 70% or more in the areas of the outer packaging sheet. In other words, the effects of the first to third aspects of the invention can be sufficiently exhibited if the curved elastic band area ratio of the aforementioned numerical value or more is retained in the triangular areas. In other words, if the curved elastic band area ratio of the aforementioned numerical value or more is retained in the triangular areas, it is possible to exhibit the effects of the first to third aspects of the invention sufficiently. The aforementioned curved elastic band area ratio is retained at least in the triangular areas on at least the front side so as to eliminate catching of the toes. The aforementioned area ratio may be lowered as the case may be, because the heels of the feet abut against the back.

According to an eighth aspect the invention, there is provided a pants type disposable diaper according to any of the first to seventh aspect of the invention, characterized in that the starting and trailing end portions of the curved elastic bands are arranged within substantially the same range as that in the widthwise direction of the joint end portions of the front and the back, in which the starting and terminal end portions of the hip elastic bands are arranged.

The invention according to the eighth aspect of the invention attains an effect similar to that of the first to seventh aspects of the invention. The starting and trailing end portions of the curved elastic bands are arranged within substantially the same range as that in the widthwise direction of the joint end portions of the front and the back, in which the starting and terminal end portions of the hip elastic bands are arranged. When the user wears the pants type disposable diaper, the action force at the time of grasping and pulling up the front or the back is transmitted to the curbed elastic bands so that the crotch portion can be easily pulled up. The crotch portion of the pants type disposable diaper can be properly mounted around the crotch of the body.

Especially the curved elastic bands form the band-shaped areas, in which the elastic members are widely arranged. As a result, the action force to grasp and pull up the front or the back is easily transmitted to the curved elastic bands so that the pants type disposable diaper can be pulled up even by a lighter force. As a result, even the user having a weak arm force such as an old man can wear the pants type disposable diaper properly.

According to a ninth aspect of the invention, there is provided a pants type disposable diaper according to any of the first to eighth aspects of the invention, characterized in that the curved elastic members arranged in the outer packaging sheet are cut and made discontinuous in the range where they overlap the absorber.

The invention according to the ninth aspect of the invention attains an effect similar to that of any of the first to eighth aspects of the invention of the invention. The curved elastic members arranged in the outer packaging sheet are cut and made discontinuous in the range where they overlap the absorber. As a result, the curbed elastic bands applies no shrinking force to the absorber.

In short, the curved elastic members do not shrink the absorber. As a result, the absorber is hardly deformed but can absorb the bodily fluid such as urine satisfactorily thereby to reduce the leakage of the bodily fluid.

According to a tenth aspect of the invention, there is provided a pants type disposable diaper according to the ninth aspect of the invention, characterized in that the curved elastic members are cut at positions generally along the side edge shaping lines of the absorber.

In the invention according to the tenth aspect of the invention, the curved elastic members are cut and made discontinuous on the absorber (not the absorbent body), and the curved elastic members are cut at positions generally along the side edge shaping lines of the absorber. By varying the cut positions of the curved elastic members in conformity with the side edge shape of the absorber, the tensions of the elastic members can be effectively kept while preventing the shrinkage of the absorber, so that the absorber can be closely held on the body.

According to an eleventh aspect of the invention, there is provided a pants type disposable diaper according to any of the first to eighth aspects of the invention, characterized in that the curved elastic members are fixed in the transverse area over at least the absorbent body with an adhesive, which is applied at a vertical spacing to the outer packaging sheet to form a plurality of rows along the horizontal direction, in that the ratio between the spacing width of the adhesive and the spacing width between the curved elastic members in the adhesive spacing width direction is set by integral multiples, and in that the curved elastic members are cut and made discontinuous over the absorbent body on lines along the longitudinal direction of the diaper.

In the eleventh aspect of the invention, the curved elastic members are fixed in the transverse area over at least the absorbent body so as to cut the elastic members thereby to prevent the shrinkage of the absorber under the condition of the bead application method using the adhesive, which is applied at the vertical spacing to the outer packaging sheet to form the plural rows along the horizontal direction, in that the ratio between the spacing width of the adhesive and the spacing width between the curved elastic members in the adhesive spacing width direction is set by integral multiples. As a result, the intersecting portions between the curved elastic members and the adhesive lines are arranged on the lines along the longitudinal direction of the diaper. If the curved elastic members are cut over the absorbent body on the lines along the longitudinal direction of the diaper, the fixed points of the curved elastic members are uniformly arranged.

According to a twelfth aspect of the invention, there is provided a pants type disposable diaper according to any of the first to eleventh aspects of the invention, characterized in that the hip elastic members are cut and made discontinuous over the absorber.

In the invention according to the twelfth aspect of the invention, the hip elastic members are cut and made discontinuous over the absorber. As a result, it is possible to prevent the shrinkage of the absorber reliably in the widthwise direction.

According to a thirteenth aspect of the invention, there is provided a pants type disposable diaper according to any of the first to twelfth aspect of the invention, characterized in that such one of the curved elastic members arranged on the side of the front as is the closest to the crotch portion and such one of the curved elastic members arranged on the side of the back as is the closest to the crotch portion are close to each other without intersecting with each other at the crotch portion.

In the thirteenth aspect of the invention, such one of the curved elastic members arranged on the side of the front as is the closest to the crotch portion and such one of the curved elastic members arranged on the side of the back as is the closest to the crotch portion are close to each other without intersecting with each other at the crotch portion. In the crotch portion, therefore, the absorbent body is pushed into close contact with the body side under a homogeneous pressure by the curved elastic members so that the clearance from the body can be sealed to exhibit a high leakage preventing effect.

According to the fourteenth aspect of the invention, there is provided a pants type disposable diaper according to any of the first to thirteenth aspects of the invention, characterized in that the hip elastic members are fixed to the outer packaging sheet by an adhesive applied to the peripheries of the elastic members, and in that the curved elastic members are fixed on the area, in which at least the hip elastic members are arranged, not by applying an adhesive to the peripheries of the curved elastic members but by the adhesive applied to the peripheries of the hip elastic members at the portions where the intersect with the hip elastic members.

In the fourteenth aspect of the invention, the hip elastic members are fixed to the outer packaging sheet by the control seam method using the adhesive applied to the peripheries of the elastic members, and the curved elastic members are fixed on the area, in which at least the hip elastic members are arranged, not by applying an adhesive to the peripheries of the curved elastic members but by the adhesive applied to the peripheries of the hip elastic members at the portions where the intersect with the hip elastic members. At the body side portions, in which the elastic members are dense, therefore, the using amount and range of the adhesive can be minimized to prevent the sheet from being hardened by the adhesive, thereby to give a softness.

According to the invention, as has been described in detail, it is possible to provide a pants type disposable diaper, which can be worn easily and properly.

BRIEF DESCRIPTION OF THE DRAWINGS

FIGS. 19(A) to 19(C) are diagrams showing modifications of the cutting method of the invention.

DETAILED DESCRIPTION OF THE INVENTION

An embodiment of the invention is described in the following with reference to FIG. 1 to FIG. 7.

Figure 1:
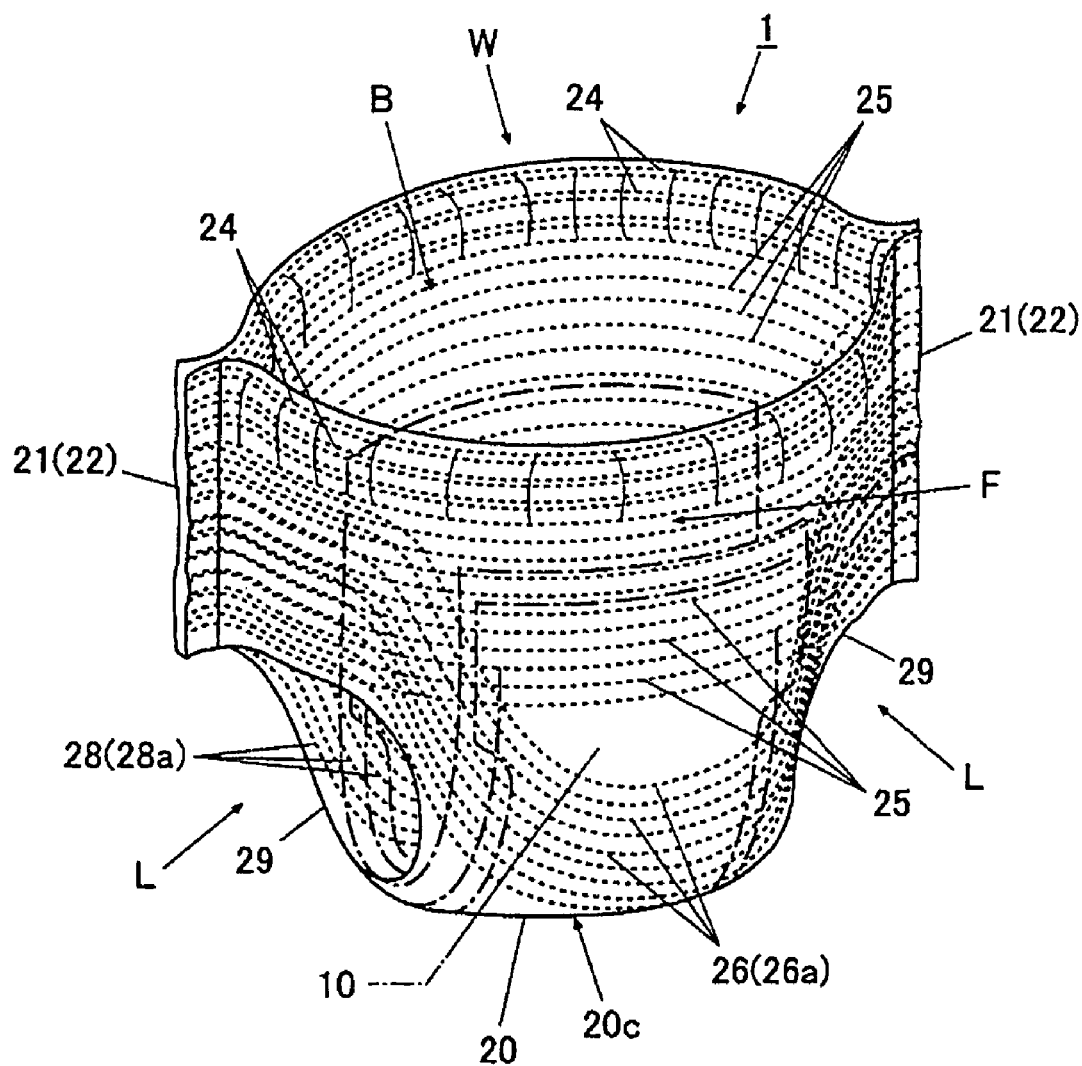
FIG. 1 is an exterior view in its final manufactured state of a pants type disposable diaper according to the invention.
Figure 2:
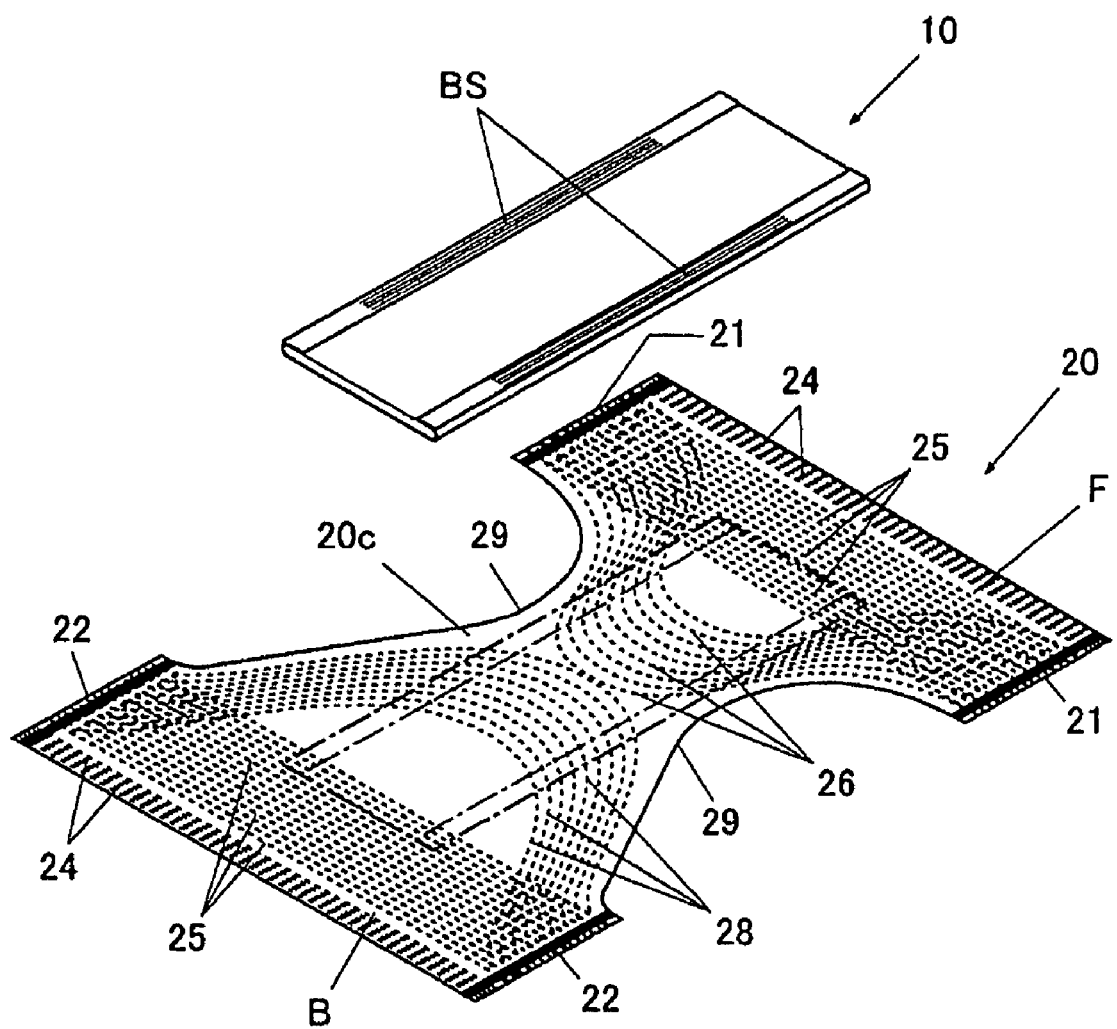
FIG. 2 is an assembly diagram in an expanded state of the paper diaper.
Figure 3:
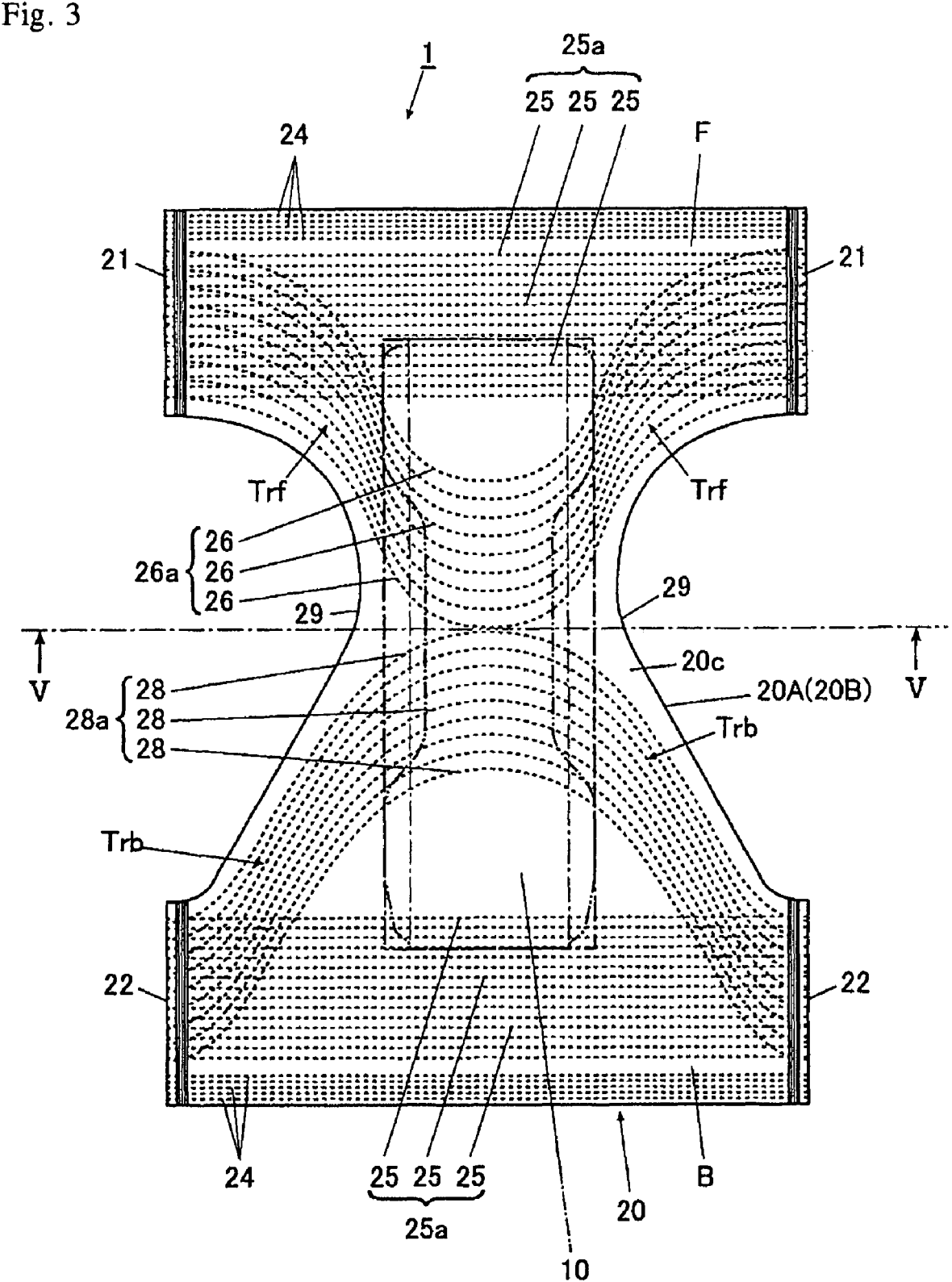
FIG. 3 is an expansion diagram of an outer packaging sheet.
Figure 6:
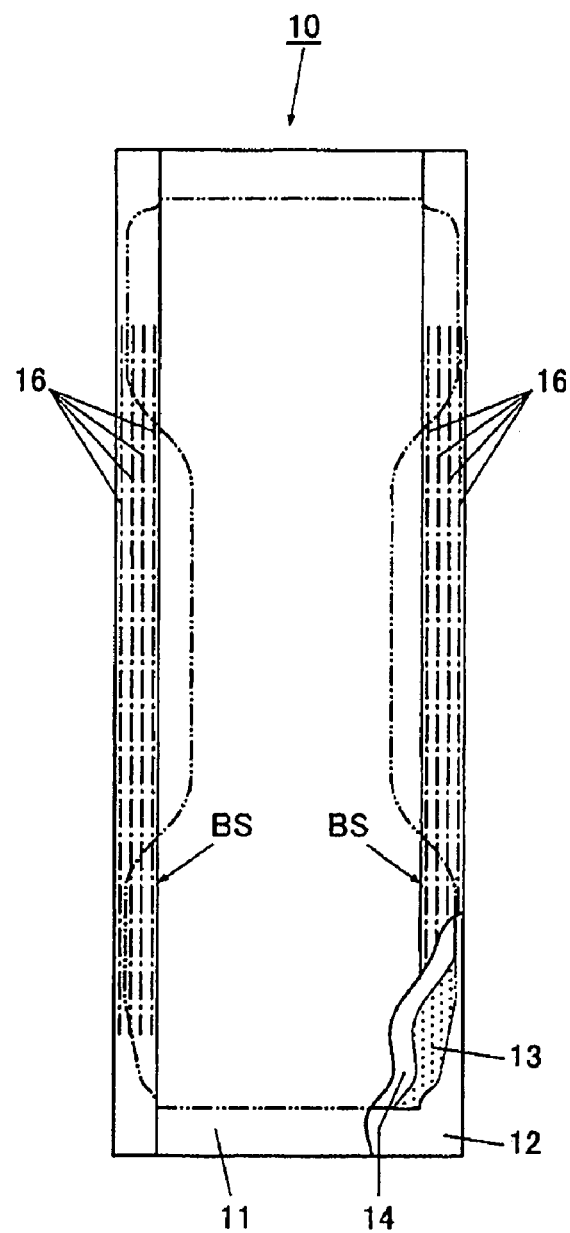
FIG. 6 is a top plan view of an absorbent body.
Figure 7:
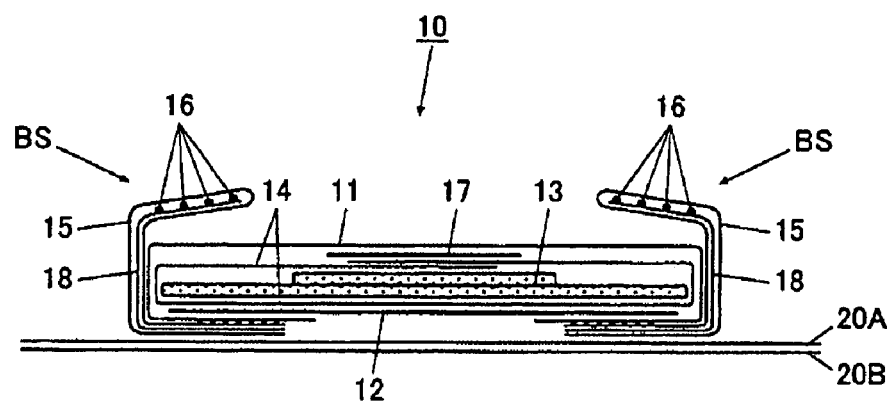
FIG. 7 is a sectional diagram along line V-V of FIG. 3.

FIG. 1 is an exterior view in its final manufactured state of a pants type disposable diaper according to the invention; FIG. 2 is an assembly diagram in an expanded state; and FIG. 3 is an expansion diagram of an outer packaging sheet. FIG. 6 is a top plan view of an absorbent body belonging to the pants type disposable diaper, and FIG. 7 is a sectional diagram along line V-V of FIG. 3.

As shown in FIG. 1 to FIG. 7, a pants type disposable diaper 1 (as will be called the "paper diaper 1") is provided with an absorbent body 10 containing an absorber 13, and an outer packaging sheet 20 disposed integrally with the outer side of the absorbent body 10. A front F on the front end side of a crotch portion 20c in the outer packaging sheet 20 in the product state and a back B on the back end side of that crotch portion 20c are jointed at joint end portions (21 and 22) on their two side ends thereby to form a waist opening W positioned around the waist of a wearer, and a pair of left and right leg openings L, through which the legs of the wearer are threaded.

In this paper diaper 1, as shown in FIG. 2, the outer side of the absorbent body 10 is adhered by an adhesive such as a hot melt to the upper side of the outer packaging sheet 20 or the body side at the paper diaper wearing time, thereby to integrate the absorbent body 10 and the outer packaging sheet 20. Moreover, the front F and the back B of the outer packaging sheet 20 are folded up by folding the crotch portion 20c of the outer packaging sheet 20 together with the absorbent body 10, and the joint end portions 21 and the joint end portions 22 are jointed at their left and right to each other by a solvent welder, a hot-melt welding agent or ultrasonic waves hereby to assemble the paper diaper 1, as shown in FIG. 1.

(Absorbent Body)

As shown in FIG. 6 and FIG. 7, the absorbent body 10 has a structure, in which the absorber 13 made of cotton pulp or a highly water-absorptive resin is sandwiched between a liquid-permeable surface sheet 11 of a nonwoven fabric and a leakage-preventing sheet 12 of polyethylene or the like, and can absorb and hold the bodily fluid.

Moreover, the absorbent body 10 has a pair of stereo gathers BS stretching in the longitudinal direction along the side edge portions of the absorbent body 10.

The absorber 13 is formed to have a general hourglass shape, for example, in a top plan view, and such a width as to given no stiff feel when it abuts against the body of the wearer.

Moreover, the absorber 13 is enclosed by a crape paper 14 so as to improve the shape holding property and the diffusivity of the bodily fluid having passed through the liquid-permeable surface sheet 11. Moreover, a second sheet 17 is sandwiched between the crape paper 14 and the liquid-permeable surface sheet 11. Here, the absorber 13 may be exemplified by an air-laid absorber, which can be less bulky.

The liquid-permeable surface sheet 11 for covering the surface side (or the skin abutting side) of the absorber 13 is preferably exemplified by a porous or non-porous nonwoven fabric or a porous plastic sheet. The material fibers composing the nonwoven fabric can be exemplified not only by synthetic fibers of an olefin family such as polyethylene or polypropylene, a polyester family, or a polyamide family but also by regenerated fibers such as rayon or cuprammonium rayon, or natural fibers such as cotton. The nonwoven fabric can be prepared by a suitable working method such as a spun lace method, a spun bond method, a thermal bond method, a melt-blown method or a needle punch method. Of these working methods, the nonwoven fabric by the spun lace method is excellent in softness and rich drape, and the nonwoven fabric by the thermal bond method is excellent in bulkiness and softness.

Moreover, the liquid-permeable surface sheet 11 can absorb, in case it is formed with numerous pores, urine or the like quickly so that it can be excellent in the dry touch.

The leakage-preventing sheet 12 covering the back side (or the skin non-abutting side) of the absorber 13 is made of a liquid-impermeable plastic sheet of polyethylene or polypropylene. In recent years, a moisture-permeable plastic sheet is preferably used from the point of preventing stiffness. This water-repellent/moisture-permeable sheet is a finely porous sheet, which is produced by melting and blending an inorganic filler into an olefin resin such as polyethylene or polypropylene thereby to form a sheet, and then by orienting the sheet uniaxially or biaxially. The finely porous sheet is superior in softness, because it is less rigid than the non-porous sheet if it has an equal sheet thickness.

This leakage-preventing sheet 12 is preferably made so opaque as to make the brown color of feces or urine hardly visible. The leakage-preventing sheet 12 is preferably made of a film, which is prepared by adding a pigment or filler such as calcium carbonate, titanium oxide, zinc oxide, white carbon, clay, talc or barium sulfate into the olefin resin or plastics.

The stereo gathers BS are formed of a gathered nonwoven fabric 15 doubled by folding it, and a waterproof sheet 18 sandwiched between the folded sheets of the gathered nonwoven fabric 15. This gathered nonwoven fabric 15 is adhered such that it further wraps the side edge portion of the absorber 13 wrapped by the liquid-permeable surface sheet 11 and extends to the back side of the absorber 13. At the longitudinally intermediate portion of the paper diaper 1 (or the absorbent body 10), more specifically, the gathered nonwoven fabric 15 is adhered over the range from the widthwise intermediate portion to the back side of the absorber 13, while leaving the portions to form the stereo gathers BS, by a hot-melt adhesive or the like. At the longitudinally front and back end portions, on the other hand, the gathered nonwoven fabric 15 is adhered over the range to the back side of the absorber 13 at the section from the widthwise intermediate portion to one side end portion, while the portions to form the stereo gathers BS being folded on the upper face portion of the absorber 13, by the hot-melt adhesive or the like.

Inside of the gathered nonwoven fabric 15 doubly folded, moreover, a plurality of thread-like elastically stretchable members 16, 16, . . . , and so on are arranged on the raising leading end sides of the gathers. These thread-like elastically stretchable members 16, 16, . . . , and so on are used to raise the gathered nonwoven fabric 15 by their elastically stretchable forces thereby to form the stereo gathers BS.

The thread-like elastically stretchable members 16 can be made of a material such as styrene family rubber, olefin family rubber, urethane family rubber, ester family rubber, polyurethane, polyethylene, polystyrene, styrene-butadiene, silicone or polyester. The thread-like elastically stretchable members 16 are preferably arranged to have a thickness of 300 to 1,200 dtex and a tension of 150 to 350%. Here, the thread-like elastically stretchable members may also be replaced by tape-shaped elastically stretchable members having a width of some extent.

Moreover, the material fibers composing the gathered nonwoven fabric 15 can be made, like the liquid-permeable surface sheet 11, of a nonwoven fabric exemplified not only by synthetic fibers of an olefin family such as polyethylene or polypropylene, a polyester family or a polyamide family but also by regenerated fibers such as rayon or cuprammonium rayon, or natural fibers such as cotton. The nonwoven fabric can be prepared by a suitable working method such as the spun lace method, the spun bond method, the thermal bond method, the melt-blown method or the needle punch method. It is, however, especially preferred to use the nonwoven fabric, which is made excellent in the air permeability by suppressing the weighing so as to prevent the stuffiness. Moreover, the gathered nonwoven fabric 15 may be exemplified by a water-proofed nonwoven fabric, which is coated with a waterproof material such as a silicone family, a paraffin metal family or an alkyl chromic chloride family waterproof material so as to prevent the permeation of urine and a skin rash and to enhance the feel (or dry feel) to the skin.

(Outer Packaging Sheet)

The outer packaging sheet 20 is a nonwoven fabric sheet of a two-layered structure having an upper-layer nonwoven fabric 20A and a lower-layer nonwoven fabric 20B, as shown in FIG. 1 to FIG. 3. The outer packaging sheet 20 is given stretching properties by arranging the later-described various elastic members between the upper-layer nonwoven fabric 20A and the lower-layer nonwoven fabric 20B.

Moreover, the outer packaging sheet 20 includes: the crotch portion 20c, which is formed at the two intermediate side portions with recessed leg cut lines 29 to form the leg openings L individually and which cover the crotch of the wearer of the paper diaper 1; the front F positioned on the front end side of the crotch portion 20c thereby to cover the abdomen of the wearer; and the back B positioned on the back end side of the crotch portion 20c thereby to cover the back of the wearer. The outer packaging sheet 20 forms a pseudo-sandglass shape as a whole.

Here, the front F is formed with the joint end portions 21 to be jointed to the back B, and the back B is formed with the joint end portions 22 to be jointed to the front F.

The joint end portions 21 and the joint end portions 22 are given such a vertical width individually at the front F and at the back B as extends from the opening end portion side of the waist opening W to the leg openings L having the leg cut lines 29.

This outer packaging sheet 20 is provided: individually at the front F and at the back B, with a plurality of waist elastic members 24, 24, . . . , and so on arranged on the opening end side (or the upper side) of the waist opening W; individual at the front F and at the back B, with a plurality of hip elastic members 25, 25, . . . , and so on arranged generally in parallel with each other at a vertical spacing from the opening end portion of the waist opening W toward the crotch portion 20c; at the front F, with a plurality of curved elastic members 26, 26, . . . , and so on arranged to extend from one joint end portion 21 to the crotch portion 20c and to detour the crotch portion 20c to the other joint end portion 21; and, at the back B, with a plurality of curved elastic members 28, 28, . . . , and so on arranged to extend from one joint end portion 22 to the crotch portion 20c and to detour the crotch portion 20c to the other joint end portion 22.

The waist elastic members 24 are a plurality of rubber string elastic members arranged at a vertical spacing in the vicinity of the waist opening W within the range of the vertical width of the joint end portions 21 and the joint end portions 22, at which the front F and the back B are jointed. The waist elastic members 24 apply the stretching forces to fasten the waist portion of the body thereby to mount the paper diaper 1 on the body. Here, the waist elastic members 24 may be made of not the rubber string elastic members but also tape-shaped elastic members.

The hip elastic members 25 are a plurality of rubber string elastic members arranged generally in parallel to one another at a vertical spacing over the range substantially of the vertical width of the joint end portions 21 and the joint end portions 22, at which the front F and the back B are jointed. The hip elastic members 25 apply the stretching forces to fasten the hip portions of the front F and the back B thereby to hold the paper diaper 1 in close contact with the body.

These plural hip elastic members 25, 25, . . . , and so on are arranged with a predetermined width and over a predetermined range in the outer packaging sheet 20 so that they function as hip elastic bands 25a having a predetermined width thereby to hold the whole faces of the front F and the back B more closely on the body.

Here, the boundaries between the hip elastic members 25 and the waist elastic members 24 may not necessarily be clearly defined. Of the plural elastic members arranged at a vertical spacing and generally in parallel with one another in the front F and the back B, for example, several elastic members on the upper side may function as the waist elastic members, and the remaining elastic members on the lower side may function as the hip elastic members.

The curved elastic members 26 are a plurality of, specifically at least four, preferably six or more, more preferably eight or more (e.g., nine in this mode of embodiment) rubber string elastically stretching members, which are arranged at the front F separately of the hip elastic members 25.

These plural curved elastic members 26, 26, . . . , and so on are arranged over predetermined width and range of the outer packaging sheet 20 so that they function as a curved elastic band 26a having a predetermined width.

The curved elastic band 26a is arranged to extend from one joint end portion 21 of the front F generally along the leg cut line 29 to the side of the crotch portion 20c, and to arrive at the other joint end portion 21, while detouring the crotch portion 20c, generally along the leg cut line 29 on the other side.

Moreover, the curved elastic band 26a is formed to cover such a generally triangular area Trf substantially in its entirety in the outer packaging sheet 20 as is defined by the leg cut lines 29 or the edge portions of the outer packaging sheet 20, the absorbent body 10 and the hip elastic bands 25a. Here, the coverage of the substantial entirety of the generally triangular area Trf with the curved elastic band 26a means not that the curved elastic band 26a is closely arranged in the entire area without any exception, but that the number and the area ratio of the curved elastic members 26 arranged in the triangular area Trf are larger than those in the pants type disposable diaper of the prior art.

Figure 4:
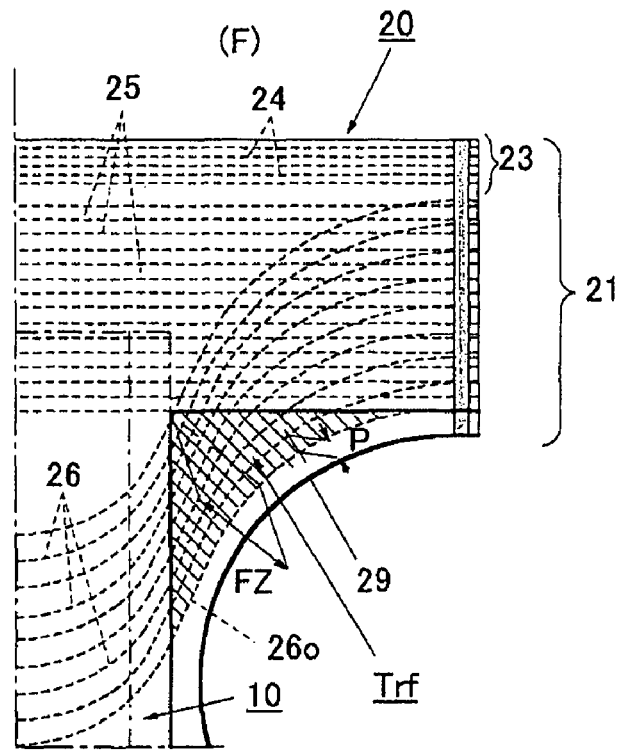
FIG. 4 is an enlarged diagram of an essential portion of a generally triangular area Trf of a front F.

In the generally triangular area Trf, as shown in FIG. 4, it is desired that the interval P of the curved elastic members 26 is 20 mm or less, preferably 15 mm or less, more preferably 9 mm or less. Moreover, it is desired that the curved elastic band 26 is formed over a range FZ of at least 30 mm or more or preferably 50 mm or more in the normal direction from such one $26_o$ of the curved elastic members 26, 26, . . . , and so on constituting the curved elastic band 26a as is the closest to the leg openings L, and that the area ratio of the area (as hatched in the drawing) of the curved elastic band 26a to the generally triangular area Trf is 70% or more.

Here, the starting and trailing end portions of the curved elastic band 26a are arranged over the substantially entire range or the vertical width of the joint end portions 21 of the front F, and in substantially the same range as that of the widthwise direction of the joint end portions 21 of the front F, in which the starting and trailing end portions of the hip elastic bands 25a are arranged.

Moreover, the curved elastic band 26a (or the curved elastic members 26) is preferred, when detouring at the crotch portion 20c, to change direction in an arcuate curve shape. The stretching force acts in the tangential direction on the elastic members. By inverting the curved elastic members 26 in the arcuate curve shape at the crotch portion 20c, therefore, the force to act in the widthwise direction of the absorbent body 10 so that the shrinkage of the absorbent body 10 in the crotch portion 20c can be reduced.

On the other hand, the curved elastic members 28 are a plurality of, specifically like the front F, at least four, preferably six or more, more preferably eight or more (e.g., nine in this mode of embodiment) rubber string elastically stretching members, which are arranged at the back B separately of the hip elastic members 25.

These plural curved elastic members 28, 28, . . . , and so on are arranged over predetermined width and range of the outer packaging sheet 20 so that they function as a curved elastic band 28a having a predetermined width.

The curved elastic band 28a is arranged to extend from one joint end portion 22 of the back B generally along the leg cut line 29 to the side of the crotch portion 20c, and to arrive at the other joint end portion 22, while detouring the crotch portion 20c, generally along the leg cut line 29 on the other side.

Moreover, the curved elastic band 28a is formed to cover such a generally triangular area Trb substantially in its entirety in the outer packaging sheet 20 as is defined by the leg cut lines 29 or the edge portions of the outer packaging sheet 20, the absorbent body 10 and the hip elastic bands 25a. Here, the coverage of the substantial entirety of the generally triangular area Trb with the curved elastic band 28a means not that the curved elastic band 28a is closely arranged in the entire area without any exception, but that the number and the area ratio of the curved elastic members 28 arranged in the triangular area Trb are larger than those in the pants type disposable diaper of the prior art.

Figure 5:
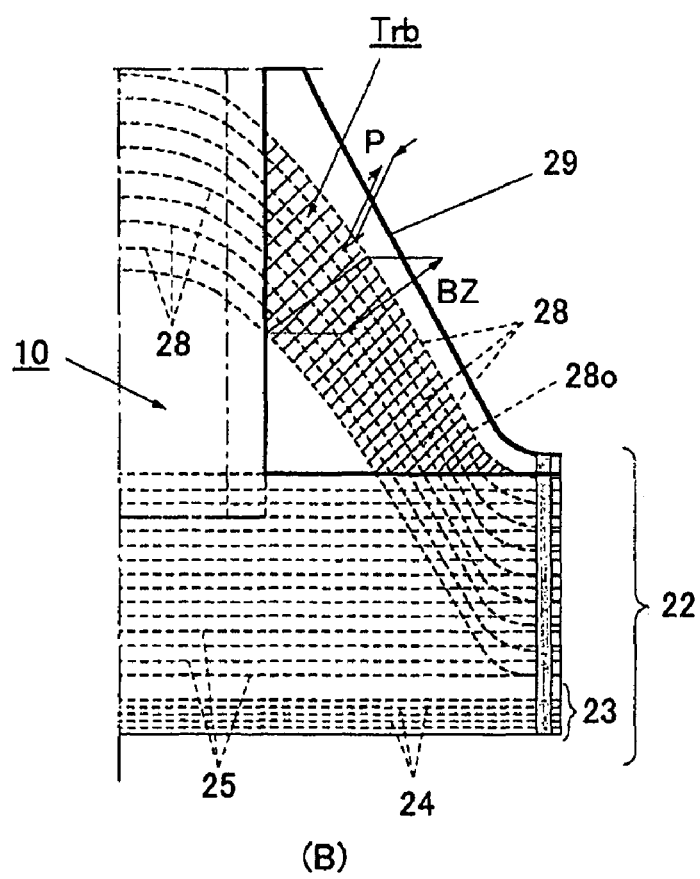
FIG. 5 is an enlarged diagram of an essential portion of a generally triangular area Trb of a back B.

In the generally triangular area Trb, as shown in FIG. 5, it is desired that the interval P of the curved elastic members 28 is 20 mm or less, preferably 15 mm or less, more preferably 9 mm or less. Moreover, it is desired that the curved elastic band 28a is formed over a range BZ of at least 30 mm or more or preferably 50 mm or more in the normal direction from such one 28, of the curved elastic members 28, 28, . . . , and so on constituting the curved elastic band 28a as is the closest to the leg openings L, and that the area ratio of the area (as hatched in the drawing) of the curved elastic band 28a to the generally triangular area Trb is 70% or more. However, the generally triangular area Trb of the back B is located on the heel side when a foot is inserted into the leg openings L. As the case may be, therefore, the area ratio may be lower than 70% but is desired to be 50% or more.

Here, the starting and trailing end portions of the curved elastic band 28a are arranged over the substantially entire range or the vertical width of the joint end portions 22 of the back B, and in substantially the same range as that of the widthwise direction of the joint end portions 22 of the back B, in which the starting and trailing end portions of the hip elastic bands 25a are arranged.

Moreover, the curved elastic band 28a (or the curved elastic members 28) is preferred, when detouring at the crotch portion 20c, to change direction in an arcuate curve shape. The stretching force acts in the tangential direction on the elastic members. By inverting the curved elastic members 28 in the arcuate curve shape at the crotch portion 20c, therefore, the force to act in the widthwise direction of the absorbent body 10 so that the shrinkage of the absorbent body 10 in the crotch portion 20c can be reduced.

Thus in the outer packaging sheet 20 of the paper diaper 1, the generally triangular area Trf is covered with the curved elastic band 26a, and the generally triangular area Trb is covered with the curved elastic band 28a. As a result, the generally triangular area Trf and the generally triangular area Trb are substantially homogeneously shrunken as a whole by the curved elastic band 26a and the curved elastic band 28a, respectively, so that those generally triangular areas Trf and Trb are prevented from bulging on their inner sides and from forming pocket-shaped spaces. If the pocket-shaped space, as would obstruct the wearing action, is not on the inner side of the paper diaper 1, the wearer hardly has, when he or she wears or removes the paper diaper 1, foot fingers or heels caught by the inner side of the paper diaper 1, so that he or she can wear the paper diaper 1 easily.

Moreover, the generally triangular area Trf and the generally triangular area Trb in the outer packaging sheet 20 of the paper diaper 1 are covered and shrunken by the curved elastic band 26a and the curved elastic band 28a, respectively, so that the outer packaging sheet 20 can be stretched to fit the bumps and dips or the bulges of the body.

In short, on the front F of the paper diaper 1, the outer packaging sheet 20 and the absorbent body 10 can be held in close contact around the urination hole of the body. On the back B of the paper diaper 1, on the other hand, the outer packaging sheet 20 can be held in close contact with the buttocks. As a result, the paper diaper 1 (or the absorbent body 10) can be more reliably held in contact with the body thereby to prevent the leakage of the bodily fluid such as urine.

Moreover, the paper diaper 1 is provided with the hip elastic bands 25a (or the hip elastic members 25) in addition to the curved elastic band 26, the curved elastic band 28a (or the curved elastic members 26 and the curved elastic members 28), so that it can be so stably mounted around the hip as to hardly slip down.

Moreover, the starting and trailing end portions of the curved elastic band 26a and the curved elastic band 28a are arranged with substantially the same range as the longitudinal range of the joint end portion 21 of the front F and the joint end portion 22 of the back B, at which the starting and trailing end portions of the waist elastic bands 25a are arranged. At the time when the user wears the paper diaper 1, the action force at the time when the front F or the back B is grasped and pulled up is transmitted to the curved elastic band 26a or the curved elastic band 28a so that the crotch portion 20c of the paper diaper 1 can be easily pulled up and properly mounted around the crotch of the body. Especially the curved elastic band 26a and the curved elastic band 28a form the band-shaped areas having the elastic members widely arranged, so that the action force to grasp and pull up the front F or the back B can be easily transmitted to the curved elastic band 26a and the curved elastic band 28a thereby to pull up the paper diaper 1 by a weaker force. As a result, even the user having a weak force such as an old person can wear the paper diaper 1 properly.

Moreover, the front F and the back B are jointed to each other by the joint end portions 21 and 22. As a result, the action force on the front F is transmitted through the back B to the curbed elastic band 28a, and the action force on the back B is transmitted through the front F to the curved elastic band 26a.

Figure 8:
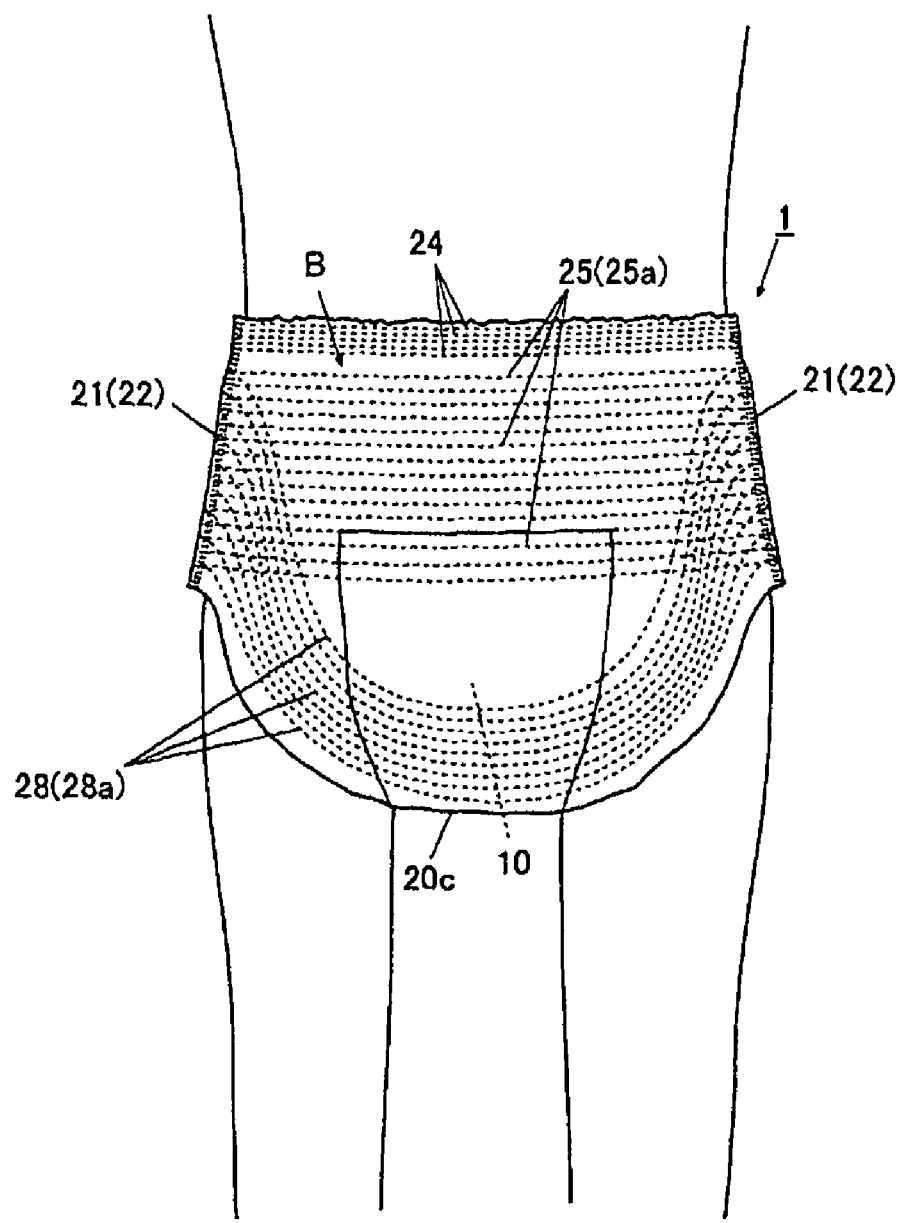
FIG. 8 is an explanatory diagram showing the state in which the pants type disposable diaper according to the invention is worn.

Even in case, moreover, the user grasps the front F with his or her single hand and pulls up the paper diaper 1, the action force on the front F is transmitted through the joint end portions 21 and 22 to the curved elastic band 28a of the back B, as shown in FIG. 8, and the paper diaper 1 can be so pulled up that the back B covers the buttocks properly. Thus, the paper diaper 1 can be satisfactorily worn around the waist.

Especially the curved elastic band 28a is curved to the crotch portion 20c so that the absorbent body 10 on the side of the crotch portion 20c can be so reliably held in close contact with the buttocks as to pull the absorbent body 10 of the crotch portion 20c closer to the buttocks thereby to prevent the leakage of the bodily fluid such as the urine.

Moreover, the paper diaper 1 is easily pulled up to fit the waist so that its incomplete wearing can be reduced. As a result, it is possible to lighten the problems of the leakage of the bodily fluid, the uncomfortable wearing feel, the ugly looks at the wearing time, the blood flow disorder due to the pressure on the body, or the skin trouble such as the rough dry skin due to the rubbing of the body.

Thus, it can be the that the paper diaper 1 is the pants type disposable diaper, which can be properly worn.

Figure 9:
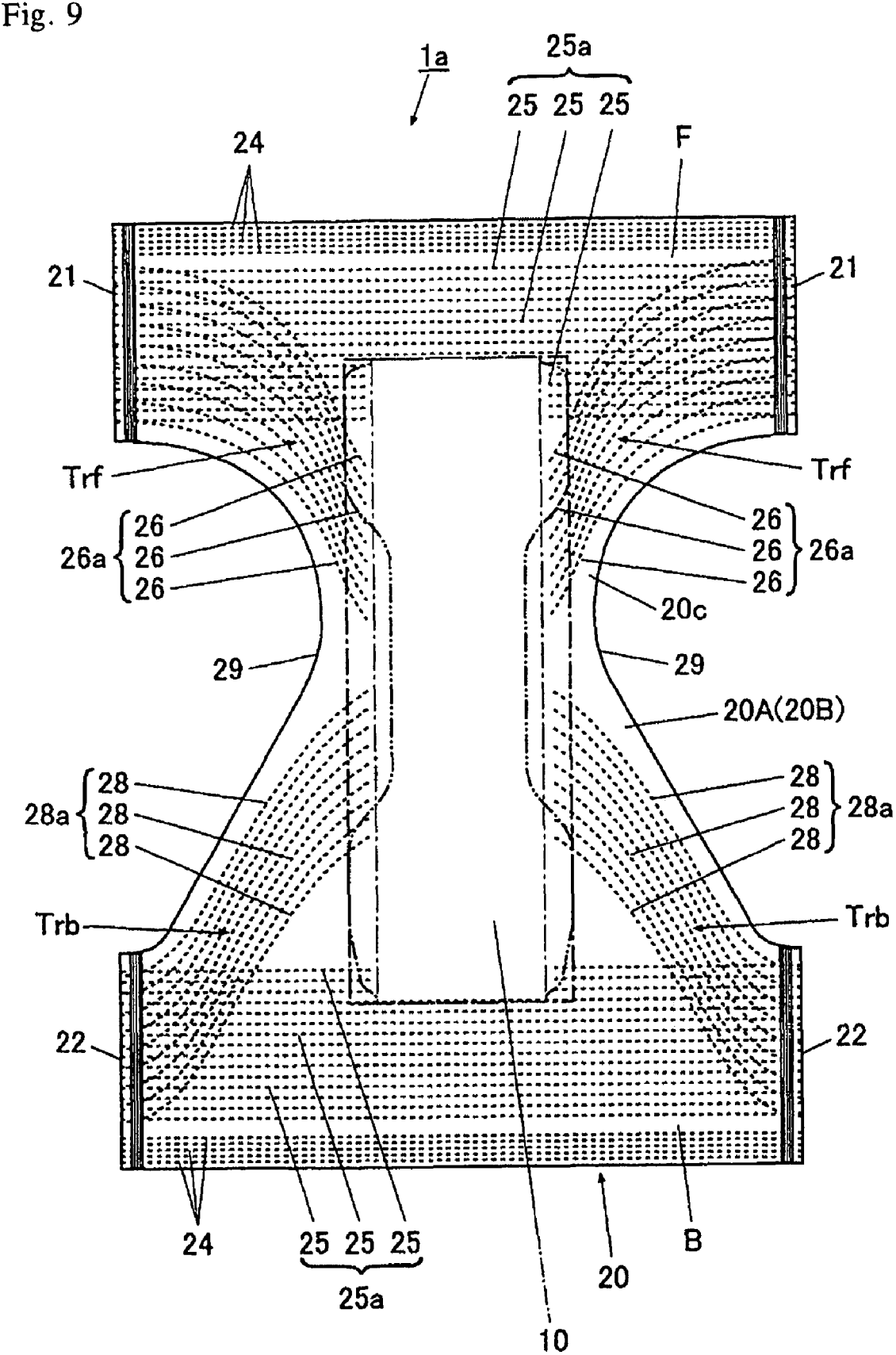
FIG. 9 is a top plan view showing a modification of the pants type disposable diaper.

In the mode of embodiment thus far described, moreover, the hip elastic bands 25a (or the hip elastic members 25), and the curved elastic band 26a and the curved elastic band 28a (or the curved elastic members 26 and the curved elastic members 28), which are arranged in the front F and the back B, are also continuously arranged in the range overlapping the absorbent body 10, especially the absorber 13. As shown in FIG. 9, the elastic members overlapping the absorbent body 10 (or the absorber 13) transversely may also be cut to discontinue. By making the elastic members discontinuous over the absorbent body 10 (or the absorber 13), it is possible to prevent the shrinkage of the absorbent body 10 (or the absorber 13). In case the curved elastic member 26, . . . , and so on, and 28, . . . , and so on are cut to discontinue over the absorber 13 (but not the absorbent body), they may be cut at the positions of the longitudinal lines, as shown in FIG. 9. Alternatively, the curved elastic member 26, . . . , and so on, and 28, . . . , and so on may also be cut at the positions generally along the side edge shaping lines of the absorber 13, that is, in a bundle shape. In case the cut positions of the curved elastic members are changed according to the side edge shapes of the absorber, the tensions of the curved elastic member 26, . . . , and so on, and 28, . . . , and so on are effectively kept while preventing the shrinkage of the absorber, so that the absorber 13 can be held in close contact with the body. Here, it is preferred that the elastic members are cut on the inner sides of 10 mm or more from the end portions of the absorber 13 (or the absorbent body 10).

Here, the arrangement is contained in the upper scope of the claim of the invention, so long as the hip elastic members 25, 25, . . . , and so on, and the curved elastic members 26, . . . , and so on, and 28, . . . , and so on are arranged in the state before cut in accordance with the regulations of the invention whether or not the elastic members are cut over the absorbent body 10.

(Fixing Method of the Elastic Members 24 to 28 and Manufacturing Method of Outer Packaging Sheet 20)

Next, the method for manufacturing the outer packaging sheet 20 is described in detail.

Figure 10:
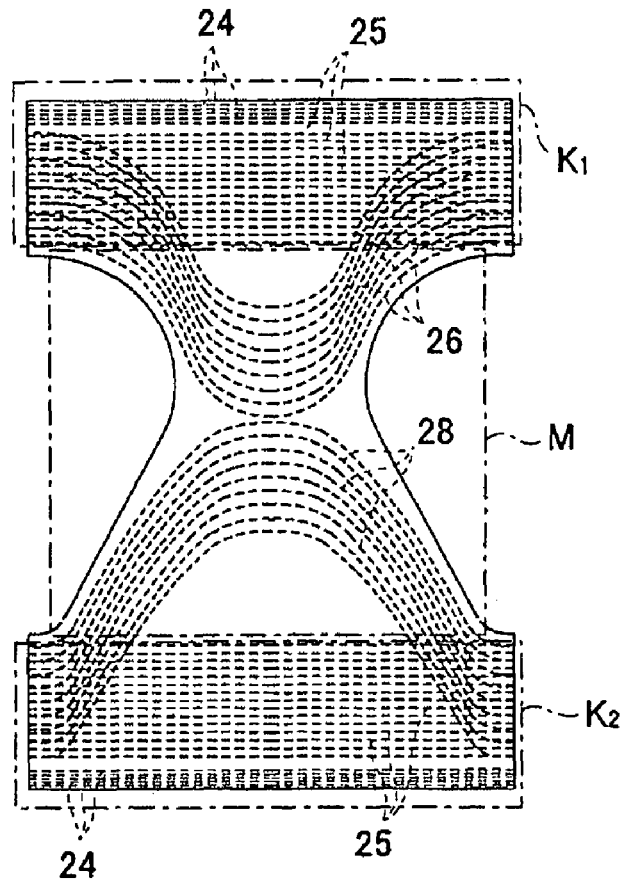
FIG. 10 is an application direction classifying diagram of the elastic members in the outer packaging sheet.

In this outer packaging sheet 20, as shown in FIG. 10, at hip shearing zones $K_1$ and $K_2$ the waist elastic members 24, 24, . . . , and so on, and the hip elastic members 25, 25, . . . , and so on are fixed to the outer packaging sheet 20 by the adhesive applied to the peripheries of the waist elastic members 24, 24, . . . , and so on, and the hip elastic members 25, 25, . . . , and so on. The curved elastic members 26, . . . , and so on, and 28, . . . , and so on are fixed at the portions intersecting with the hip elastic members 25, 25, . . . , and so on, without the adhesive being applied to the peripheries thereof by using the adhesive applied to the peripheries of the hip elastic members 25, 25, . . . , and so on. In an intermediate diaper zone M excepting the hip shearing zones $K_1$ and $K_2$, the curved elastic members 26, ..., and so on, and 28, ..., and so on are fixed by the adhesive applied to the nonwoven fabric 20A (or 20B) on at least one side of the outer packaging sheet 20.

Figure 11:
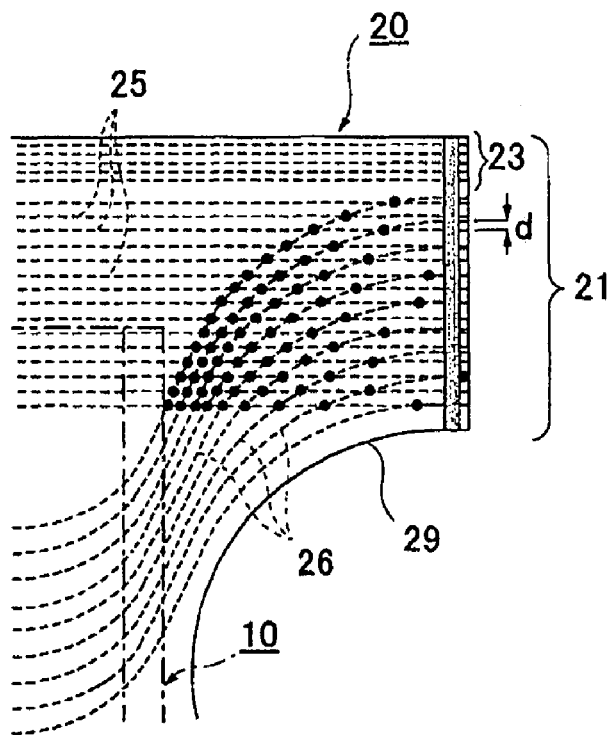
FIG. 11 is an explanatory diagram of a fixed mode of curved elastic members 28 at the side portions of an outer packaging sheet 20.

In the hip shearing zones $K_1$ and $K_2$, more specifically, the hip elastic members 25, 25, ..., and so on are fixed according to the well-known control seam method by applying the hot-melt adhesive to the peripheries of the elastic members 25 and then by introducing them into the outer packaging sheet 20. However, the abdomen side curved elastic members 26, 26, ..., and so on, and the back side curved elastic members 28, 28, ..., and so on are not fixed by applying the adhesive to their peripheries but are fixed at their portions intersecting with the hip elastic members 25, 25, ..., and so on, when they are introduced together with the hip elastic members 25, 25, ..., and so on, into the outer packaging sheet 20 by the hot-melt adhesive applied to the peripheries of the hip elastic members 25, 25, ..., and so on. As a result, at the body side portions, as shown in FIG. 11 (presenting the abdomen side portion), the abdomen side elastic members 26, 26, ..., and so on are fixed, only at their portions (as indicated by ●) intersecting with the hip elastic members 25, to the hip elastic members 25 (and to the outer packaging sheet 20 as the adhesive spreads). At the body side portions, in which the elastic members 25, ..., and so on, 26, ..., and so on, and 28, ..., and so on are dense, therefore, the using amount and range of the adhesive can be minimized to prevent the sheet from being hardened by the adhesive, thereby to give a softness.

In this case, in the two side portions in which the front F and back B of the outer packaging sheet are jointed, it is desired that the spacing distance d between the hip elastic members 25, 25, ..., and so on, and the curved elastic members 26, ..., and so on, and 28, ..., and so on is desired to be 1 mm or less. At the side edge portions, more specifically, the intersections between the hip elastic members 25, 25, ..., and so on, and the curved elastic members 26, ..., and so on, and 28, ..., and so on are positioned close to the side edge portions. When the two side edge corresponding positions are cut in the paper diaper manufacturing process, therefore, the retractions of the curved elastic members 26, ..., and so on, and 28, ..., and so on can be eliminated to bring their starting and trailing ends closer to the side edges.

Here, in order that the retraction of the curved elastic members 26, ..., and so on, and 28, ..., and so on may be completely eliminated at the cutting time, the hot-melt adhesive may be supplementally applied at the two side portions, at which the front F and the back B of the outer packaging sheet 20 are jointed, to a range S of 5 to 20 mm from the side edge portions of the outer packaging sheet 20 to the inner side, thereby to fix the curved elastic members 26, ..., and so on, and 28, ..., and so on to the outer packaging sheet 20 with the hot-melt adhesive. In this case, as shown in FIG. 12(B), a curtain application method may be performed partially (at the area P) across the diaper cut portion (as indicated by chain lines) of the hip shearing portions.

In the intermediate diaper portion M other than the hip shearing portions, on the other hand, the hot-melt adhesive is applied to the nonwoven fabric 20A (20B) on at least one side of the outer packaging sheet 20, and the curved elastic members 26, ..., and so on, and 28, ..., and so on are fixed by introducing them on that adhesive-applied face.

Figure 12A:
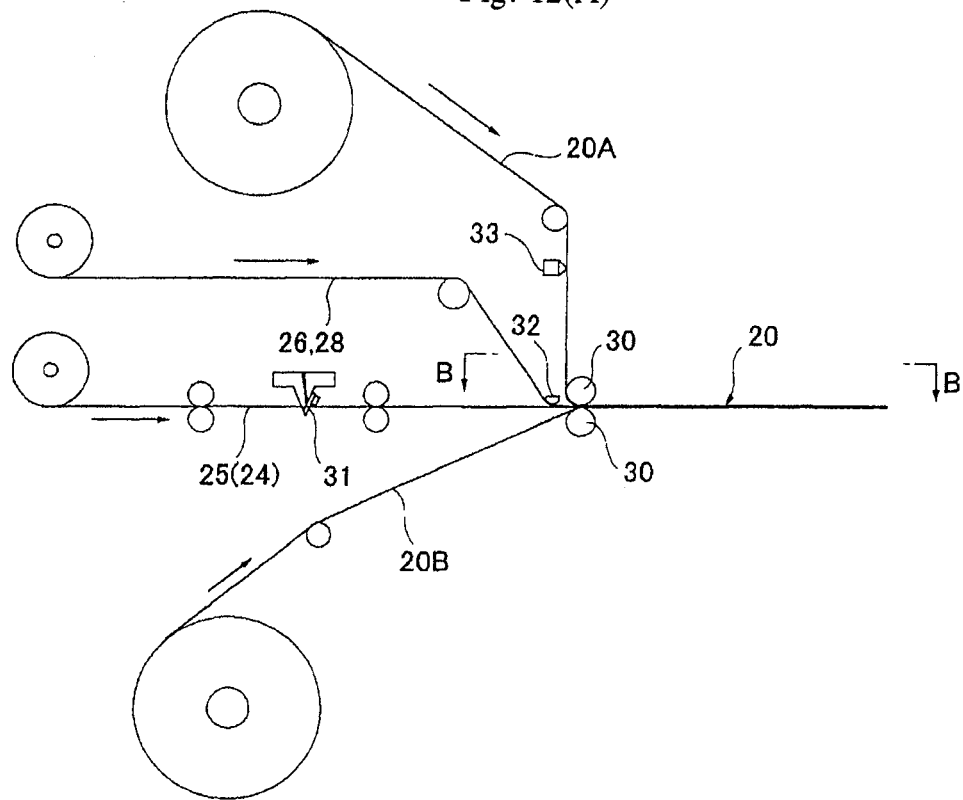
FIGS. 12(A) and 12(B) shows an assembling procedure of the outer packaging sheet 20, and presents a schematic diagram at FIG. 12(A) and an essential top plan view at FIG. 12(B).
Figure 12B:
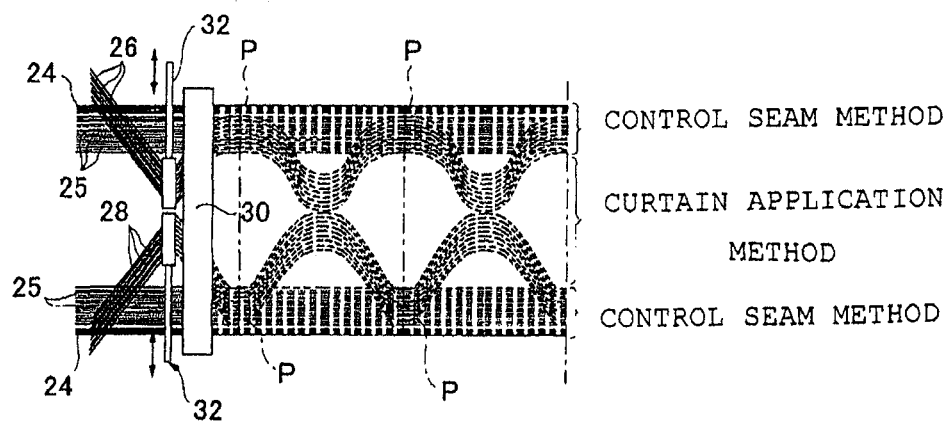

At the time of manufacturing the outer packaging sheet 20, as shown in FIG. 12, the upper-layer nonwoven fabric 20A is fed to the upper side of a nip roller unit 30, and the lower-layer nonwoven fabric 20B is fed to the lower side. The various elastic members (i.e., the waist elastic members 24, the hip elastic members 25, the abdomen side curved elastic members 26 and the back side elastic members 28) are fed to between those upper-layer nonwoven fabric 20A and lower-layer nonwoven fabric 20B. At the step of assembling the outer packaging sheet 20, for the waist elastic members 24 and the hip elastic members 25, the elastic members 24, ..., and so on, and 25, ..., and so on have the hot-melt adhesive applied to their peripheries by a periphery application device 31, and are fed to the nip roller unit 30.

Figure 13A:
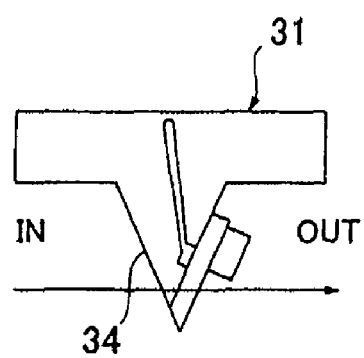
FIG. 13 presents diagrams showing application examples of an adhesive in a control seam method.
Figure 13B:
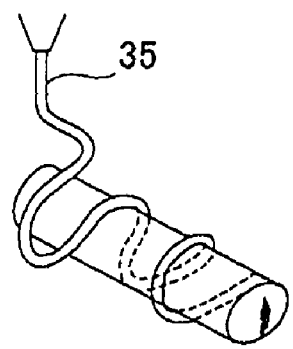
Figure 14:
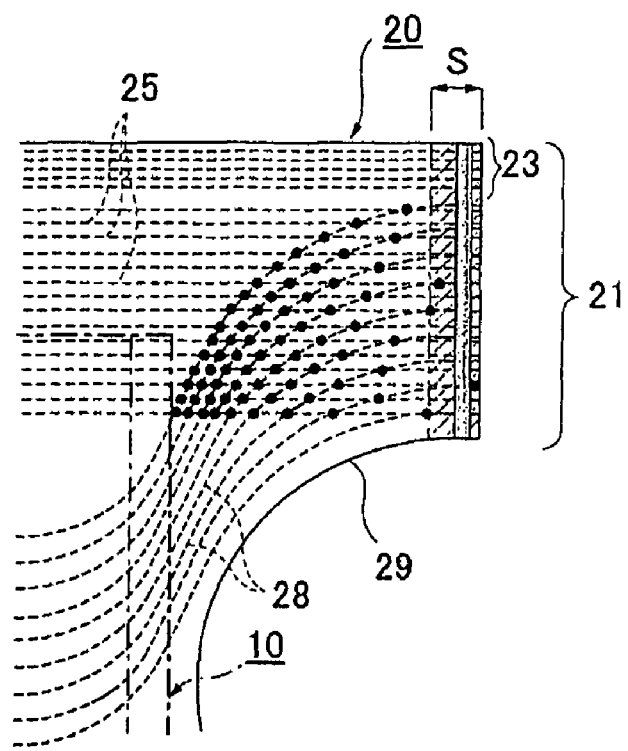
FIG. 14 is an explanatory diagram of a fixed mode (or a modification) of the curved elastic members 28 at the side portions of the outer packaging sheet 20.

The peripheral application to the curved elastic members 24, ..., and so on, and 25, ..., and so on is exemplified by: an application method according to a comb gun 31 and threading the elastic members in V-shaped grooves while feeing the adhesive to the bottom portions of the grooves by using a member 34 having the grooves, as shown in FIG. 13(A); an application method using an Ω member for applying the adhesive to the elastic members with a ring member of an omega (Ω) shape; or the control seam application method known in the prior art for passing the elastic members being entangled by a winding member 35, thereby to apply the adhesive, as shown in FIG. 13(B).

On the other hand, the curved elastic members 26, ..., and so on, and 28, ..., and so on are introduced, while being meandered by a well-known traverse device 32, into the nip roller unit 30. The traverse device 32 has holding portions of the leading end portions of the elastic members 26, ..., and so on, and 28, ..., and so on, and is moved back and forth at a calculated speed in the widthwise direction of the continuous web (i.e., the sheet 20A or 20B), so that the elastic members 26, ..., and so on, and 28, ..., and so on are arranged in a predetermined curved shape. As a result, the arranging interval of the curved elastic members 26 and 28 can be made automatically equivalent at the side joint edges 21 and 22 and the crotch portion. In the invention, the elastic members 26 and 28 are introduced without any application of the hot-melt adhesive to their peripheries, and are fixed in the hip shearing portions at the portions intersecting with the hip elastic members 25, 25, ..., and so on with the adhesive applied to the peripheries of the hip elastic members 25, 25, ..., and so on.

The hot-melt adhesive is curtain-applied by a coater 33 to at least one side in the upper-layer nonwoven fabric 20A and the lower-layer nonwoven fabric 20B, that is, the area corresponding to the intermediate diaper zone M other than the hip shearing portions of the upper-layer side nonwoven fabric 20A in the shown example, so that the curved elastic members 26, ..., and so on, and 28, ..., and so on are fixed at the intermediate diaper zone M with the hot-melt adhesive applied to the upper-layer nonwoven fabric 20A.

Here, the hot-melt adhesive is exemplified by an EVA family, an adhesive rubber family (or an elastomer family), an olefin family, or polyester-polyamide family, but it is desired that the adhesive rubber family (or the elastomer family).

Here, in the intermediate diaper zone M other than the hip shearing portion, the hot-melt adhesive is homogeneously applied in a curtain shape to an elastic member arranged area on the sheet side, and an elastic member is introduced and fixed on the adhesive. In the case of this method, the sheet may become so hard as to deteriorate the wearing feel. In recent years, therefore, there is proposed a method (as will be called the "bead application method"), in which the adhesive is applied in plural rows at a predetermined spacing thereby to fix the elastic members.

Figure 20:
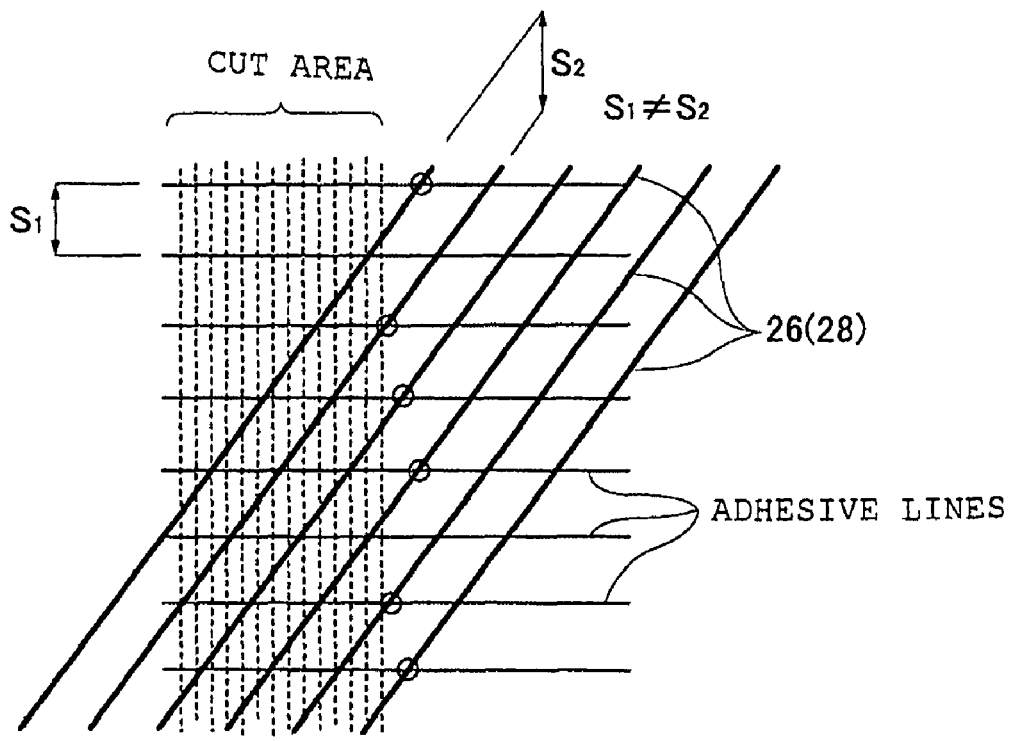
FIG. 20 is a diagram for explaining the problems of the curved elastic members cutting method of the prior art.
Figure 20:
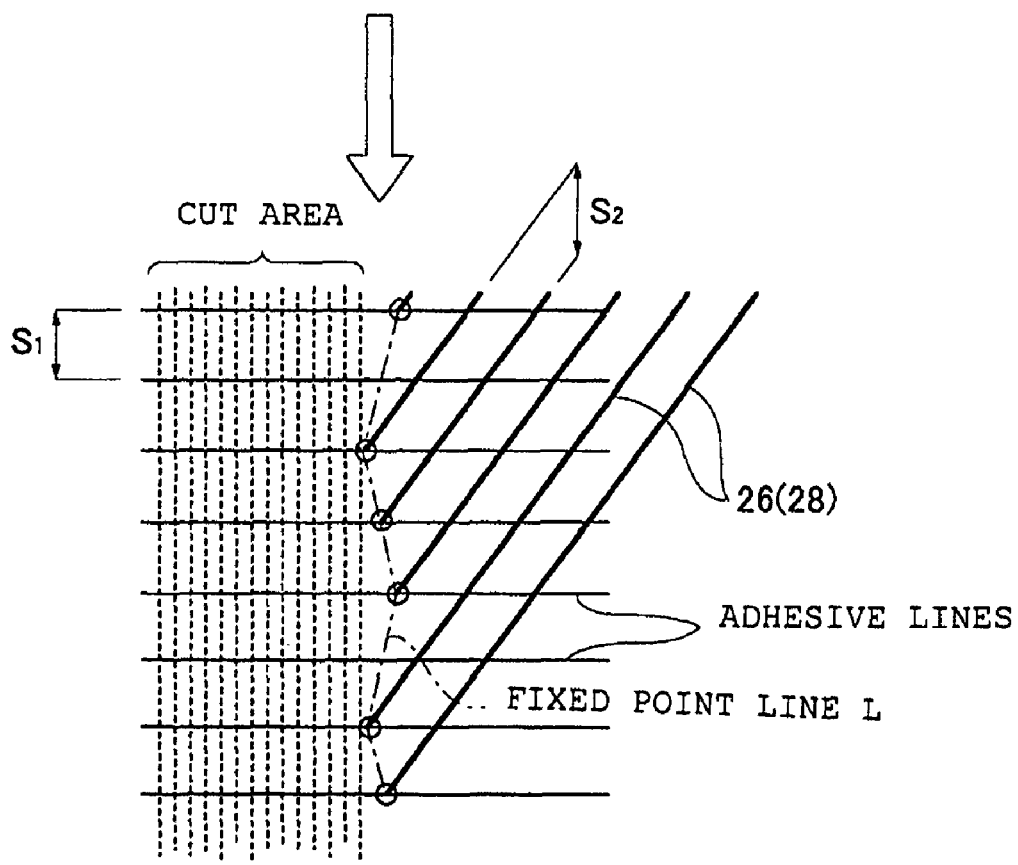
Figure 21:
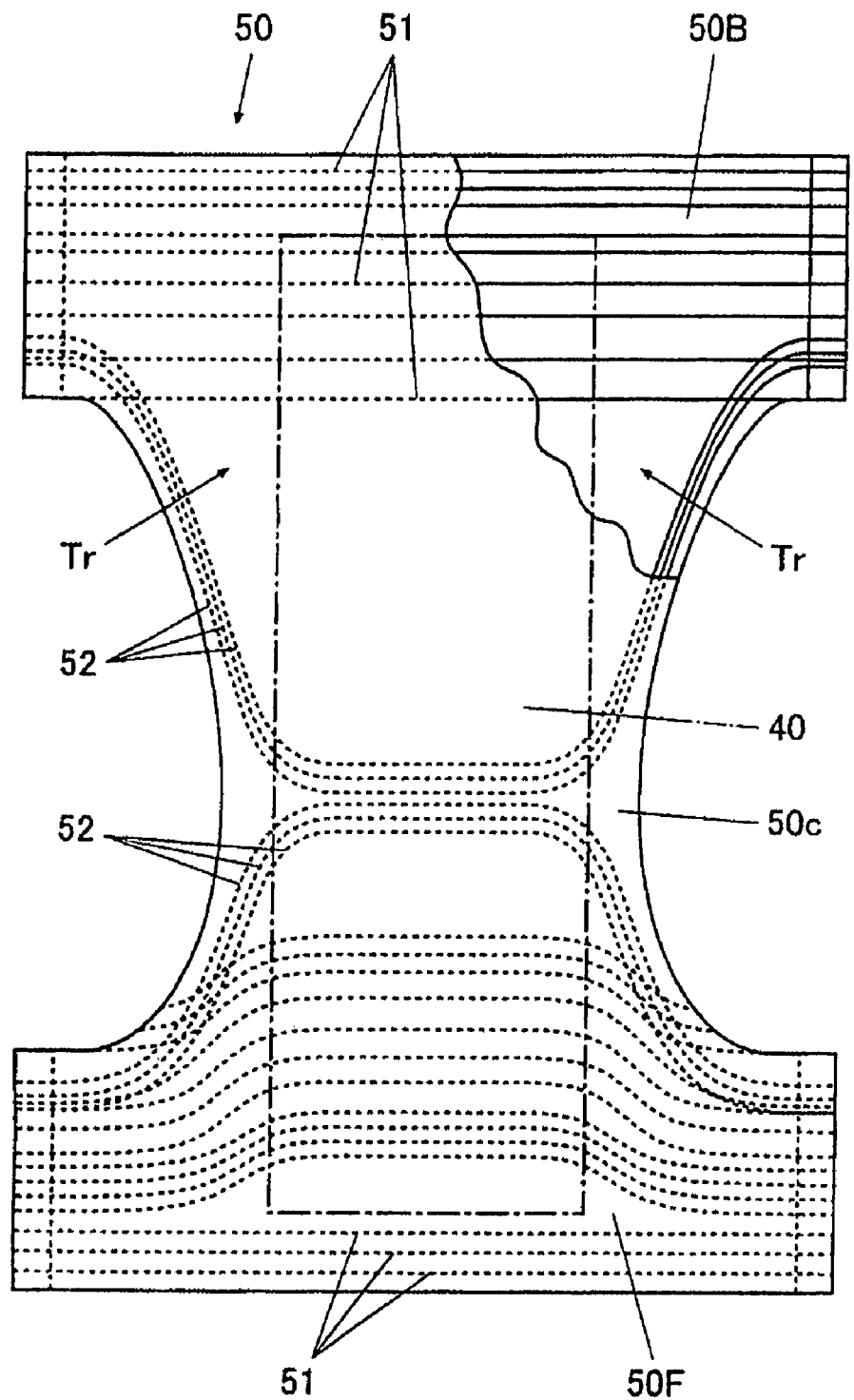
FIG. 21 is an explanatory diagram showing the disposable diaper of the related art.
Figure 22:
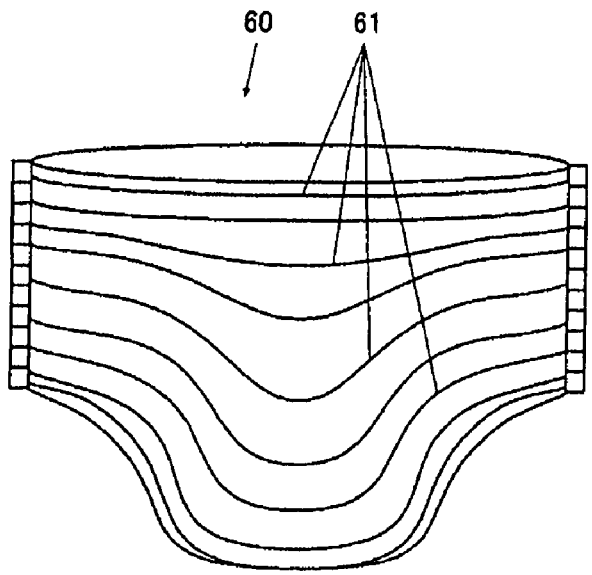
FIG. 22 is an explanatory diagram showing the disposable diaper of the related art.
Figure 23:
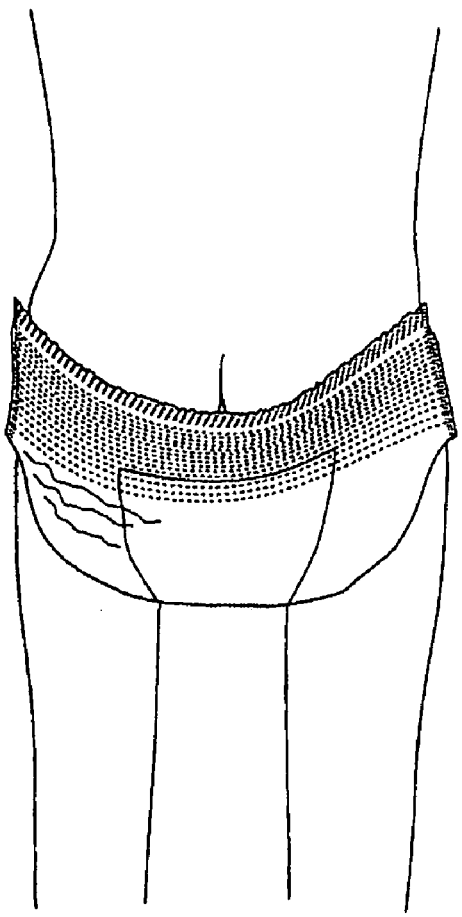
FIG. 23 is an explanatory diagram showing the state in which the pants type disposable diaper of the related art is worn.

As shown in FIG. 20, however, there is a problem that the fixed points (or the fixed point lines L) of the elastic members are not justified but zigzagged when the elastic members are cut on the absorber so as to eliminate the shrinkage of the absorber under the conditions of adopting the bead application method. This problem raises problems not only that the fitness of the absorber is deteriorated and that the absorber is wrinkled but also that the appearance is deteriorated.

The following methods can be suitably adopted to cut and discontinue the elastic members across the absorbent body 10 with solving the above problems.

Figure 15A:
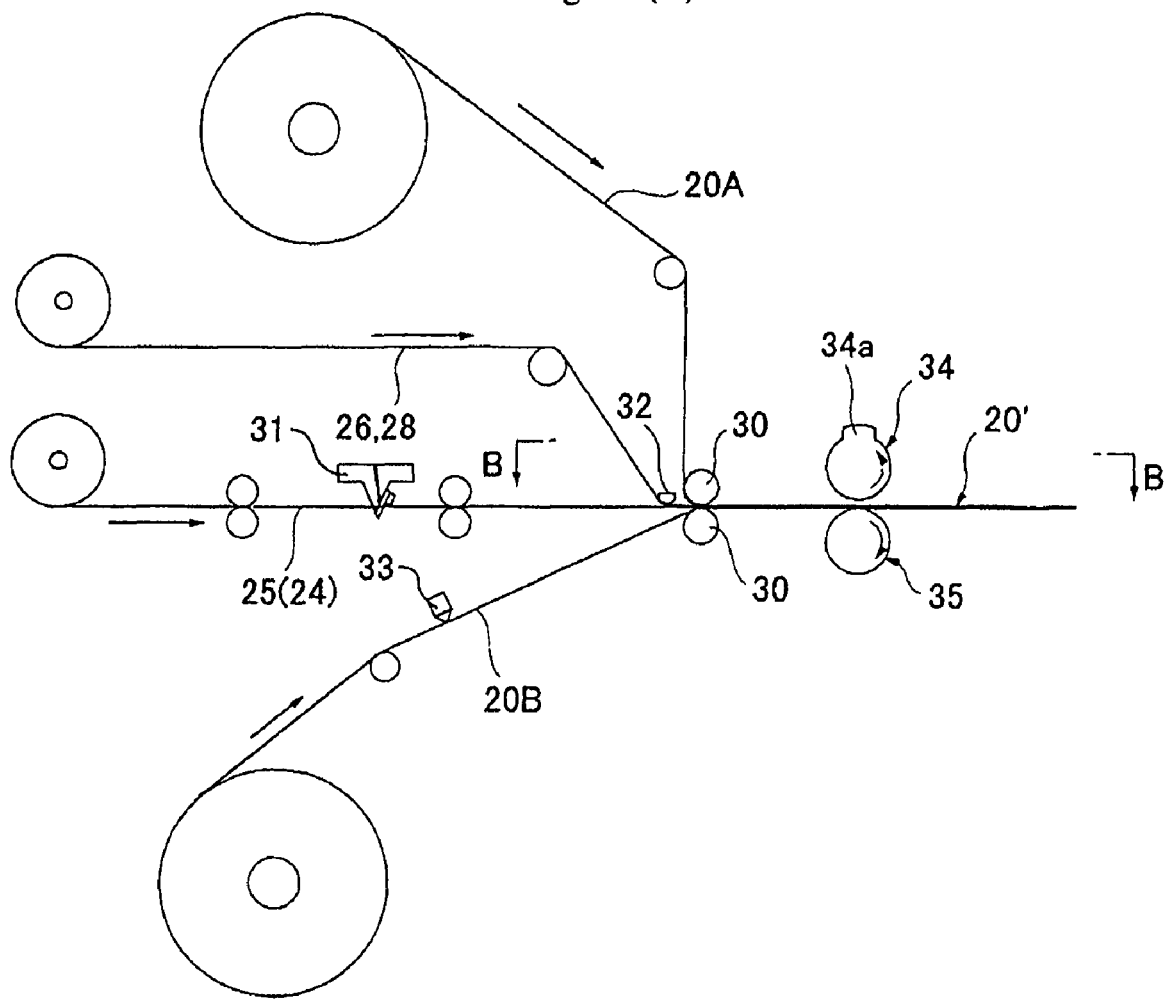
FIGS. 15(A) and 15(B) shows an assembling procedure of the outer packaging sheet 20 of the case, in which the curved elastic members are cut on the absorber, and presents a schematic diagram at FIG. 15(A) and an essential top plan view at FIG. 15(B).
Figure 15B:
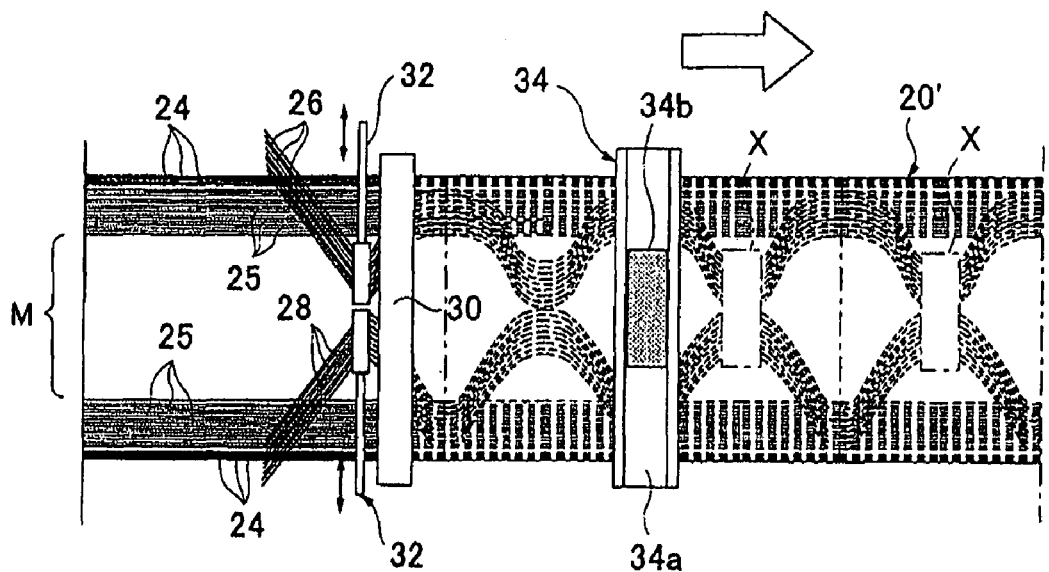

For the manufacture of the outer packaging sheet 20, as shown in FIG. 15, the outer packaging sheet 20 is continuously assembled such that the upper-layer nonwoven fabric 20A is fed to the upper side of the nip roller unit 30 whereas the lower-layer nonwoven fabric 20B to the lower side, and such that the various elastic members (e.g., the waist elastic members 24, the hip elastic members 25, the abdomen side curved elastic members 26 and the back side elastic members 28) are fed to between those upper-layer nonwoven fabric 20A and the lower-layer nonwoven fabric 20B.

For fixing the waist elastic members 24 and the hip elastic members 25 to the sheets, the peripheries of the elastic members 24, . . . , and so on, and 25, . . . , and so on have the hot-melt adhesive applied to their peripheries by the periphery application device 31, and are fed to the nip roller unit 30.

For the intermediate zone M between the hip elastic members 25, 25, . . . , and so on of the front and the hip elastic members 25, 25, . . . , and so on of the back, on the other hand, at least one of the upper-layer nonwoven fabric 20A and the lower-layer nonwoven fabric 20B, that is, the lower-side nonwoven fabric 20B in the shown example are subjected to the bead application by the coater 33 in a manner to form the plural rows at the vertical spacing and along the horizontal direction. The curved elastic members 26, . . . , and so on, and 28, . . . , and so on are fixed in the intermediate zone M by the hot-melt adhesive applied to the lower-layer nonwoven fabric 20B.

In order to cut and discontinue of the curved elastic members 26, . . . , and so on, and 28, . . . , and so on on the absorbent body 10, the cutting method, as described in JP-A-2002-35029, JP-A-2002-178428 and JP-A-2002-273808 is properly adopted. In the elastic member cutting method described, as basically shown in FIG. 15, a laminate sheet 20' to become the outer packaging sheet 20 is manufactured and is then passed between the emboss heat roll 34 having plural projections arrayed on its surface and the opposed roll 35 confronting the emboss heat roll 34 so that the curved elastic members 26, . . . , and so on, and 28, . . . , and so on of the laminate sheet 20' are cut by pressing and/or heating them between the projections of the emboss heat roll 34 and the opposed roll 35. Here, the X areas in FIG. 15(B) indicate the cut ranges.

Figure 16A:
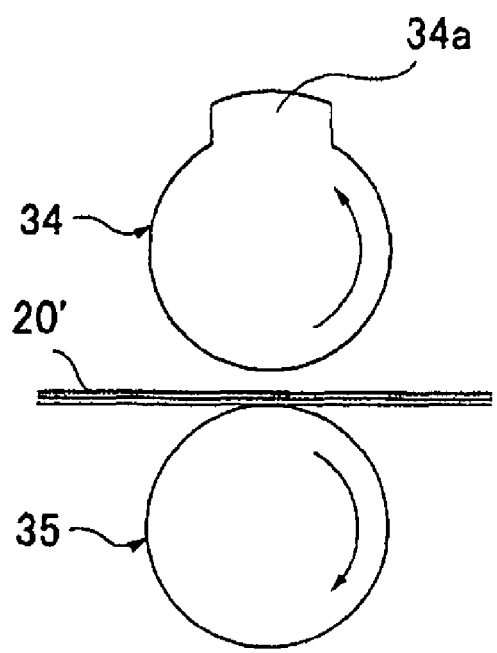
FIG. 16 is an explanatory view of an action mode of an emboss heat roll and an opposed roll.
Figure 16B:
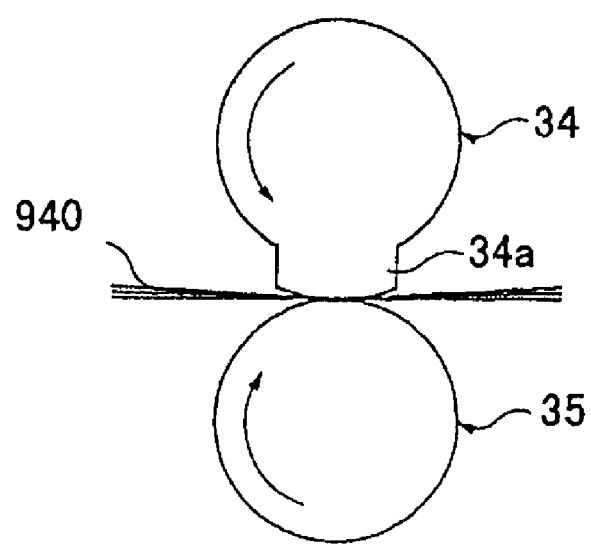

The opposed roll 35 may be so spaced from the emboss heat roll 34 as to abut against only the emboss portions 34a of the emboss heat roll 34, as shown in FIG. 16(a). As these two rolls rotate, the emboss portion 34a moves downward to abut against the opposed roll 35, as shown in FIG. 16(b). Here on the surface of the emboss portion 34a, small projections 40 to 43, as shown in FIG. 17, for example, are further formed in an hourglass shape on a defining area 34b. As a matter of fact, those projections 40 to 43 come at their leading end faces into abutment against the opposed roll 35.

Figure 17A:
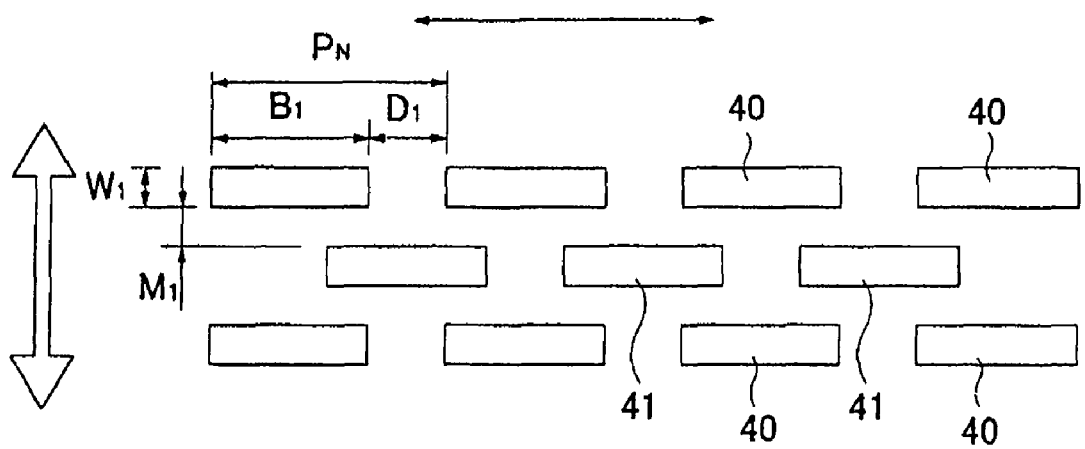
FIGS. 17(a) and 17(b) are explanatory diagrams showing examples of emboss patterns of staggered arrays.
Figure 17B:
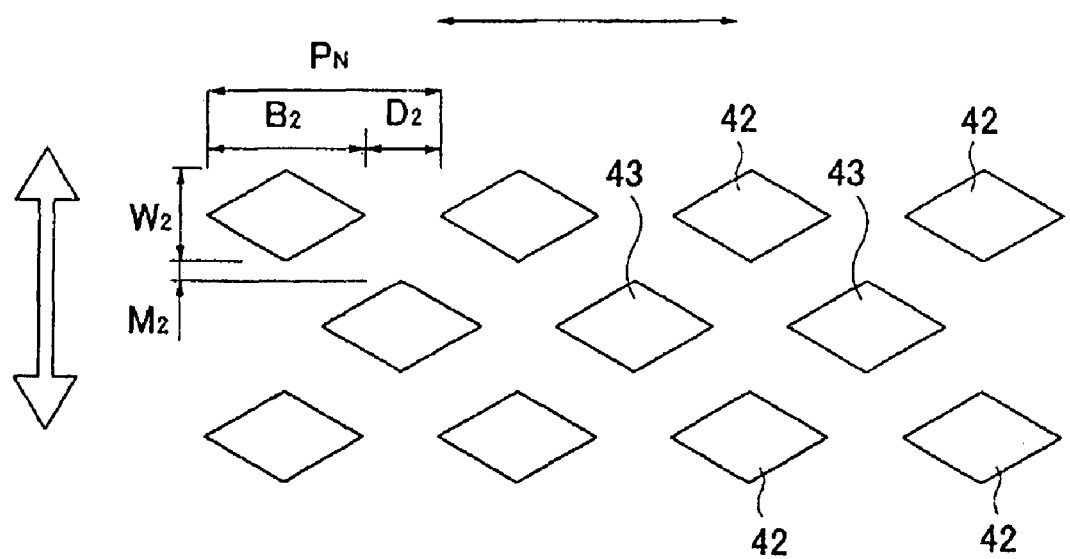

The preferred examples of the emboss pattern are shown in FIGS. 17(a) and 17(b). FIG. 17(a) shows an emboss pattern, in which the plural linear projections are arranged in a staggered shape. In this emboss pattern, there are alternately repeated the rows of projection groups, in which the linear projections 40 having a length S1 and a width W1 are arranged at a distance D1 in the axial direction (or in the solid arrow direction) of the emboss heat roll 34, and in which the projections 41 and 41 having the same length B1 and width W1 as those of the projections 40 are so arranged at a spacing M1 from the projections 40 in the circumferential direction (or in the blank arrow direction) as that the lengthwise center lines of the projections 41 may extend through the points of 2/D1. FIG. 17(b) shows an emboss pattern, in which the rhomboid projections are arranged in a staggered shape. In this emboss pattern, there are alternately repeated the rows of projection groups, in which rhomboid projections 42 and 42 having a longer axis B2 and a shorter axis W2 are arranged at a distance D2 in the axial direction (or in the blank arrow direction) of the emboss heat roll 34, and in which the projections 43 and 43 having the same rhomboid shape as that of the projections 42 are so arranged at a spacing M2 from the projections 42 in the circumferential direction (or in the blank arrow direction) of the emboss heat roll 34 that the shorter axis of the projections 42 correspond to the points of 2/D2.

The length B1 of the linear projections and the longer axis B2 of the rhombuses preferably have a range of 1 to 25 mm, and more preferably have a range of 5 to 25 mm. Moreover, the spacing distances D1 and B1 from the adjoining projections are equal, or the distance B1 is preferably longer. Because of the staggered arrangement, the members positioned between the projections 40 and the projections 40 can be reliably cut with the projections 41. Likewise, the relation between D2 and B2 is preferably D2≦B2. If B1 or B2 is shorter than 1 mm, the elastic members may be unable to be cut. If longer than 25 mm, the area of the sealing portion may become so large as to deteriorate the skin feel. Therefore, the range of D1 and D2 is preferably within 1 to 25 mm, and the range D1 is more preferably within 3 to 25 mm. In the case of the rhomboid projections, if the corners of the projections adjoining in the circumferential direction of the roll overlap only slightly, as viewed in the laying direction of the elastic members, the elastic members may leave the sealing portion so that they cannot be cut. Thus, D2 is more preferably within 3 to 10 mm.

The width W1 of the linear projections and the shorter axis W2 of the rhombuses is preferably 0.5 to 15 mm. If thinner than 0.5 mm, the elastic members may be unable to be cut. If thicker than 15 mm, the area of the sealing portion may be too large to give a good skin feel. The axis W2 preferably has a lower limit of 1 mm or more.

The distance between the rows of the projection groups is not especially limited, but the spacing M1 or M2 is preferably 5 to 25 mm. The shapes of the projections should not be limited the aforementioned linear or rhomboid shape but can be exemplified by oblique lines, circles, triangles, stars or other polygons. Also, the shapes can be modified by each of the rows of the projections.

Figure 18:
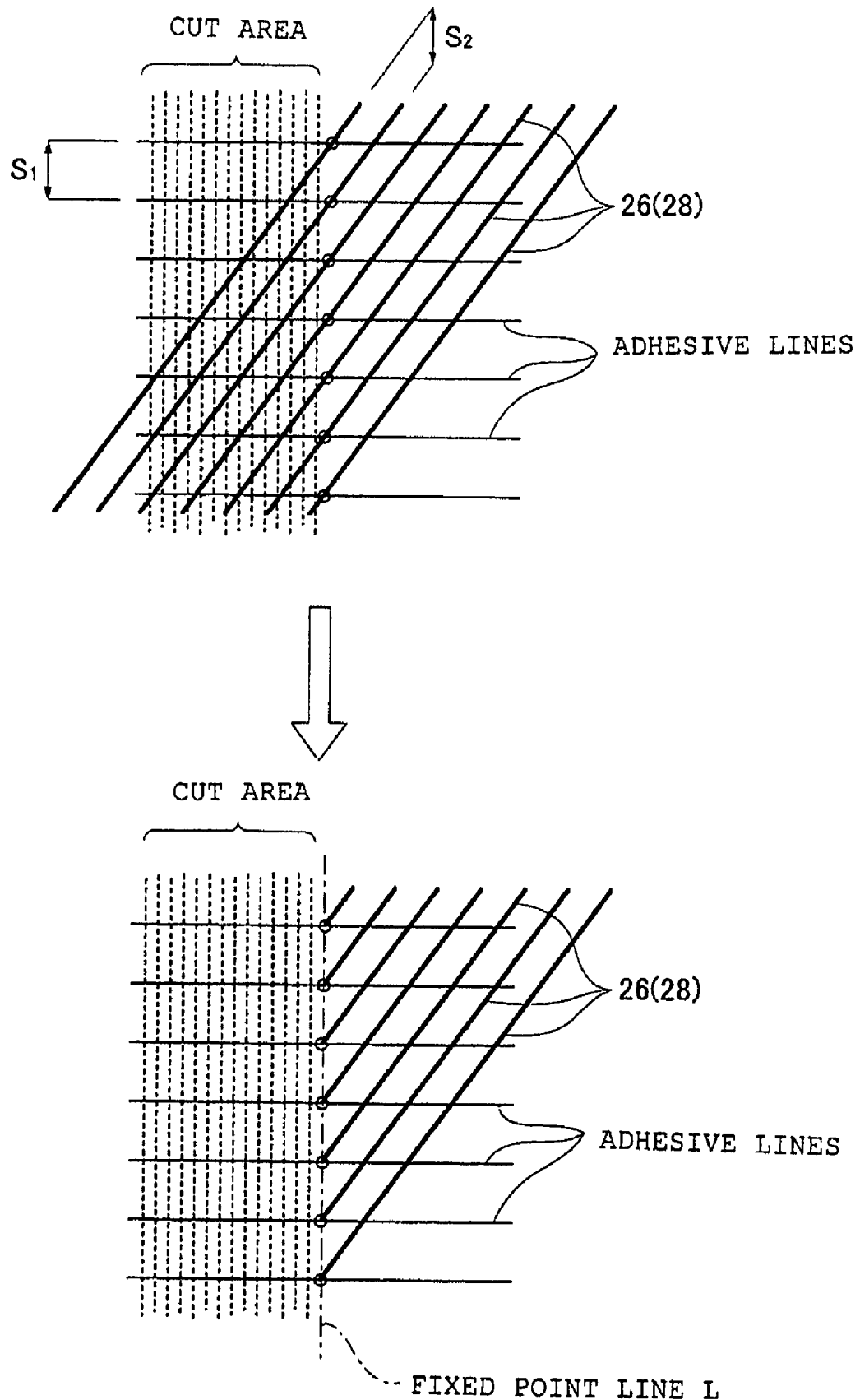
FIG. 18 is an explanatory diagram showing a method of cutting curved elastic members 26, . . . , and so on, and 28, . . . , and so on according to the invention.

In the present disposable diaper, when the curved elastic members 26, . . . , and so on, and 28, . . . , and so on are cut and discontinued on the absorbent body 10, their fixed points are arranged substantially on a common line in the longitudinal direction of the diaper. For this arrangement, as shown in FIG. 18, the ratio between a spacing width $S_1$ of the adhesive and a spacing width $S_2$ in the adhesive spacing width direction between the curved elastic members 26, . . . , and so on, and 28, . . . , and so on is about several times, e.g., one in the shown example. Thus, the intersections (as indicated by ◯) between the adhesive lines and the curved elastic members 26, . . . , and so on, and 28, . . . , and so on are regulated to predetermined positions in the longitudinal direction of the diaper. If the curved elastic members are cut at line positions along the longitudinal direction of the diaper on the absorbent body 10, their fixed points are arranged on substantially identical straight lines (or the fixed point line L) in the longitudinal direction of the diaper.

Other modes of embodiment are presented. FIG. 19(A) presents an example of the case, in which the ratio between a spacing width $S_1$ of the adhesive and a spacing width $S_2$ in the adhesive spacing width direction between the curved elastic members 26, . . . , and so on, and 28, . . . , and so on is about two. Moreover, the adhesive lines should not be limited to the straight beads, but may also be applied in a spiral shape to form plural rows as a whole, as shown FIG. 19(B), or may be applied in an undulating shape by a summit spray to form plural rows as a whole.

(Assembling of Paper Diaper)

The absorbent body 10 and the outer packaging sheet 20 are integrated, as shown in FIG. 2, such that the absorbent body 10 is adhered to the upper face side of the outer packaging sheet 20 with an adhesive such as a hot melt. Then, the absorbent body 10 and the outer packaging sheet 20 are folded back and forth, and their two side portions are jointed to each other by a thermally welding method or a hot-melt adhesive.

(1) In the mode of embodiment thus far described, the curved elastic band 26a and the curved elastic band 28a cover the generally triangular areas Trf and Trb substantially as a whole. This coverage is not limited to that the curved elastic band 26a and the curved elastic band 28a cover the generally triangular areas Trf and Trb completely as a whole thereby not to form such a pocket-shaped space inside of the paper diaper 1 as to obstruct the wearing action, but may form a pocket-shaped space if the space has a size to cause no obstruction to the wearing action. Here, the aforementioned mode of embodiment has been shown and described in the state where the curved elastic band 26a arranged on the side of the front F and the curved elastic band 28a arranged on the back B are close to each other but do not intersect with each other in the crotch portion 20c. However, the invention should not be limited thereto, but the curved elastic band 26a and the curved elastic band 28a may intersect partially with each other.

(2) Moreover, the invention should not be limited to the paper diaper 1, which is provided with the curved elastic band 26a arranged on the side of the front F and the curved elastic band 28a arranged on the side of the back B, but may be constituted to have at least one curved elastic band.

Moreover, it is natural that the remaining specific detail structures can be suitably modified.

The invention claimed is:

1. A pants type disposable diaper, comprising:
an absorbent body, including an absorber and an outer packaging sheet formed integrally on the outer face side of the absorbent body, the outer packaging sheet comprising hip elastic bands and curved elastic bands;
wherein the outer packaging sheet has a crotch portion for covering an area around a wearer's crotch, a front portion for covering a frontal portion of a wearer and a back portion for covering a backside portion of the wearer, the absorbent body being disposed in an area passing from the front portion to the back portion through the crotch portion;
wherein the outer packaging sheet has leg cut lines at side edges to provide respective left and right leg openings, each of the front portion and the back portion being jointed at joint end portions at left and right sides thereof away from the crotch portion to form a waist opening when joined;
wherein the outer packaging sheet has a first triangle area at said front portion extending to a side of said crotch portion that is generally delimited by the leg cut line for one leg, a nearest lateral edge portion of the absorber, and a lower portion of a nearest one of the hip elastic bands;
wherein the hip elastic bands include a plurality of hip elastic members extending from one of the joint end portions toward another of the joint end portions, respectively, for each of the front portion and the back portion of the outer packaging sheet, the hip elastic members at each of the front portion and back portion, respectively, being arranged generally in parallel at a vertical spacing;
wherein the curved elastic bands include a plurality of curved elastic members extending from left joint end portions and right joint end portions toward respective sides of the crotch portion while curving to a general contour of corresponding leg cut lines;
wherein the plurality of curved elastic members have a spacing of 9 mm or less, are formed over an area of at least 30 mm in a direction normal to curved elastic members closest to the leg opening for each leg opening, cover the outer packaging sheet with an area coverage ratio of 70% or more, multiple curved elastic members of the plurality of curved elastic members covering the entire first triangle area at said coverage area ratio of 70% or more; and
wherein the hip elastic members are fixed to the outer packaging sheet with adhesive applied around the hip elastic members, and the curved elastic members are fixed, without adhesive applied around the curved elastic members at least in the area where the hip elastic members are arranged, in an intersection with the hip elastic members by the adhesive applied around the hip elastic members.

2. The diaper of claim 1, wherein each member of the plurality of hip elastic members is arranged to have a starting or an ending point at any one joint end portion of the joint end portions, said starting or ending points being within a widthwise range at said any one joint end portion, and wherein each member of the plurality of curved elastic members is arranged to have a starting or an ending point at any one joint end portion of the joint end portions, said curved elastic member starting or ending points being within the same widthwise range as hip elastic member starting or ending points at the same joint end portion.

3. The diaper of claim 2, wherein the outer packaging sheet further comprises a plurality of waist elastic members, wherein at each one joint end portion, an innermost and outermost curved elastic member have either one of their starting or ending points at a same widthwise range position as an uppermost and lowermost hip elastic member, respectively.

4. The diaper of claim 1, wherein each one curved elastic member among the plurality of curved elastic members at said front portion is formed to extend continuously from one of either the left or right joint end portion to the other of said left or right joint end portion.

5. The diaper of claim 1, wherein each one curved elastic member among the plurality of curved elastic members at said back portion is formed to extend continuously from one of either the left or right joint end portion to the other of said left or right joint end portion.

6. The diaper of claim 1, wherein each one curved elastic member among the plurality of curved elastic members at said front portion starting at said left joint end portion has a corresponding one curved elastic starting at said right joint end portion, each one curved elastic member and its corresponding curved elastic member extending to form a discontinuous elastic member, where the discontinuation occurs along a width portion of the absorber.

7. The diaper of claim 6, wherein for each said discontinuous elastic member, said one curved elastic member extends to and discontinues along one side edge shaping line of the absorber and said corresponding curved elastic member extends to and discontinues along another side edge shaping line of the absorber.

8. The diaper of claim 1, wherein each one curved elastic member among the plurality of curved elastic members at said back portion starting at said left joint end portion has a corresponding one curved elastic starting at said right joint end portion, each one curved elastic member and its corresponding curved elastic member extending to form a discontinuous elastic member, where the discontinuation occurs along a width portion of the absorber.

9. The diaper of claim 8, wherein for each said discontinuous elastic member, said one curved elastic member extends to and discontinues along one side edge shaping line of the absorber and said corresponding curved elastic member extends to and discontinues along another side edge shaping line of the absorber.

10. The diaper of claim 1, wherein each one curved elastic member among the plurality of curved elastic members at said front portion starting at said left joint end portion has a corresponding one curved elastic starting at said right joint end portion, each one front portion curved elastic member and its corresponding curved elastic member extending to form a front portion discontinuous elastic member, where the discontinuation occurs along a width portion of the absorber;
wherein each one curved elastic member among the plurality of curved elastic members at said back portion starting at said left joint end portion has a corresponding one curved elastic starting at said right joint end portion, each one back portion curved elastic member and its corresponding curved elastic member extending to form a back portion discontinuous elastic member, where the discontinuation occurs along a width portion of the absorber.

11. The diaper of claim 10, wherein for each said front portion discontinuous elastic member and each said back portion discontinuous elastic member, said one curved elastic member extends to and discontinues along one side edge shaping line of the absorber and said corresponding curved elastic member extends to and discontinues along another side edge shaping line of the absorber.

12. The diaper of claim 1, wherein first curved elastic members are fixed with an adhesive in at least a transverse area over the absorbent body at a vertical spacing to the outer packaging sheet so as to form a plurality of rows along a horizontal direction, and the ratio between a spacing width of the adhesive and a spacing width between the first curved elastic members in the adhesive spacing width direction is an integral multiple, and the first curved elastic members are discontinuous over the absorbent body on lines along the longitudinal direction of the diaper.

13. The diaper of claim 1, wherein hip elastic members among the plurality of hip elastic members that overlap the absorber are discontinuous over the absorber.

14. The diaper of claim 1, wherein the curved elastic members on the front portion do not intersect with any of the curved elastic members on the back portion.

15. The diaper of claim 1, wherein the curved elastic member on the front portion that is closest to the back portion and the curved elastic member on the back portion that is the closest to the front portion are positioned close to each other without intersecting with each other.

16. The diaper of claim 1, wherein the hip elastic bands are fixed to the outer packaging sheet by an adhesive applied to peripheries of the hip elastic members and the curved elastic bands are fixed on the area in which at least the hip elastic members are arranged by an adhesive applied to the peripheries of the hip elastic members at the portions intersecting with the hip elastic members.

* * * * *